United States Patent [19]

Sprecker et al.

[11] Patent Number: 4,924,026
[45] Date of Patent: May 8, 1990

[54] TRIISOBUTYLENE ALCOHOLS AND ESTERS, USES THEREOF IN PERFUMERY AND HALOGENATED INTERMEDIATES USEFUL FOR PREPARING SAME

[75] Inventors: Mark A. Sprecker, Sea Bright; Robert P. Belko, Woodbridge; Marie R. Hanna, Keyport, all of N.J.

[73] Assignee: International Flavors & Fragrances Inc., New York, N.Y.

[21] Appl. No.: 392,423

[22] Filed: Aug. 11, 1989

[51] Int. Cl.$^5$ .......................................... C07C 69/007
[52] U.S. Cl. ................................. 560/261; 568/857; 568/909.5; 568/877; 568/858; 560/237; 570/189
[58] Field of Search ............... 560/261, 237; 568/857, 568/909.5, 877, 858; 570/189

[56] References Cited

U.S. PATENT DOCUMENTS

| | | | |
|---|---|---|---|
| 2,777,883 | 1/1957 | Chambers et al. | 260/654 |
| 4,359,412 | 11/1982 | Boden | 252/522 R |
| 4,420,411 | 12/1983 | Boden et al. | 252/174.11 |

FOREIGN PATENT DOCUMENTS 56-135431 10/1981 Japan .............................. 568/909.5

OTHER PUBLICATIONS

Chem. Abstracts, vol. 66:45942n.

Primary Examiner—James H. Reamer
Attorney, Agent, or Firm—Arthur L. Liberman

[57] ABSTRACT

Described are triisobutylene alcohols and esters and halogenated intermediates for preparing same defined according to the generic structure:

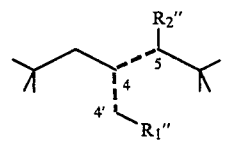

wherein one of the dashed lines represents a carbon-carbon single bond and the other of the dashed lines represents a carbon-carbon double bond; wherein $R_1''$ and $R_2''$ are the same or different and each represents hydrogen, chloro, bromo, hydroxyl or a $C_1$–$C_3$ acyloxy with the provisos that when the dashed line in the 4—4' position is a carbon-carbon double bond then $R_1''$ is hydrogen and $R_2''$ is not hydrogen, and $R_1''$ and $R_2''$ are not both hydrogen.

Also described are the uses of the triisobutylene alcohols and esters in augmenting or enhancing the aroma of perfume compositions, colognes and perfumed articles including but not limited to perfumed polymers solid or liquid anionic, cationic, nonionic or zwitterionic detergents, fabric softener compositions, fabric softener articles, cosmetic powders and hair preparations.

7 Claims, 12 Drawing Sheets

GLC PROFILE FOR EXAMPLE I.

FIG. 2 NMR SPECTRUM FOR PEAKS 101 & 121, EXAMPLE I.

NMR SPECTRUM FOR PEAK 141, EXAMPLE I.

GLC PROFILE FOR EXAMPLE II.

FIG. 5 NMR SPECTRUM FOR PEAKS 41 & 43, EXAMPLE II.

FIG. 6. NMR SPECTRUM FOR PEAKS 45 & 47 OF EXAMPLE II.

GLC PROFILE FOR EXAMPLE III.

FIG. 8 NMR SPECTRUM FOR PEAKS 70 & 72, EXAMPLE III.

NMR SPECTRUM

NMR SPECTRUM

TRIISOBUTYLENE ALCOHOLS AND ESTERS, USES THEREOF IN PERFUMERY AND HALOGENATED INTERMEDIATES USEFUL FOR PREPARING SAME

BACKGROUND OF THE INVENTION

This invention relates to triisobutylene alcohols and esters defined according to the generic structure:

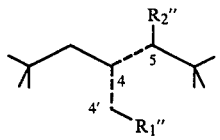

wherein one of the dashed lines is a carbon-carbon double bond and the other of the dashed lines is a carbon-carbon single bond; wherein $R_1''$ and $R_2''$ are the same or different and each represents hydrogen, hydroxyl or $C_1$–$C_3$ acyloxy with the provisos that $R_1''$ and $R_2''$ are not both hydrogen and when the carbon-carbon bond at the 4—4' position is a carbon-carbon double bond, then $R_1''$ is hydrogen and uses thereof in augmenting or enhancing the aroma of perfume compositions, colognes and perfumed articles.

Inexpensive chemical compositions of matter which can provide myrrh-like, olibanum-like, balsamic, peppery, fruity, rose, geranium, herbaceous, woody and linseed oil-like aromas with myrrh, olibanum, honey-like, fruity, ozoney, leathery, fresh, peppery, rose, geranium, minty and green topnotes and leathery undertones are highly desirable in the art of perfumery. Many of the natural materials which provide such fragrances and contribute desired nuances to perfumery compositions as well as perfumed articles including solid or liquid anionic, cationic, nonionic or zwitterionic detergents, fabric softener compositions and fabric softener articles are high in cost, vary in quality from one batch to another and/or are generally subject to the usual variations of natural products.

There is, accordingly, a continuing effort to find synthetic materials which will replace, enhance or augment the essential fragrance notes provided by natural essential oils or compositions thereof. Unfortunately, many of the synthetic materials either have the desired nuances only to a relatively small degree or else contribute undesirable or unwanted odor to the compositions. The search for materials which can provide a more refined myrrh-like, olibanum-like, balsamic, peppery, fruity, rose, geranium, herbaceous, woody and linseed oil-like aroma, with myrrh, olibanum, honey-like, fruity, ozoney, leathery, fresh, peppery, rose, geranium, minty and green topnotes and leathery undertones has been difficult and relatively costly in the areas of both natural products and synthetic products.

Acylated derivatives of triisobutylene defined according to the generic structures:

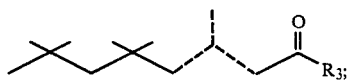

-continued

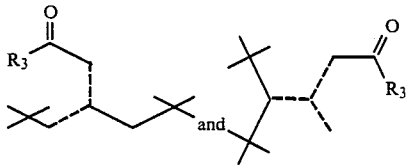

wherein, in each of the molecules one of the dashed lines represents a carbon-carbon double bond and each of the other of the dashed lines represents a carbon-carbon single bond; and wherein, in each of the molecules $R_3$ represents methyl or ethyl for use in augmenting or enhancing the aroma of perfume compositions, colognes and perfumed articles.

Furthermore, U.S. Pat. No. 4,359,412 describes a genus of compounds defined according to the structure:

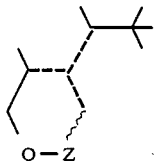

wherein one of the dashed lines represents a carbon-carbon double bond and each of the other of the dashed lines represent a carbon-carbon single bonds; wherein the wavy line ∼∼∼∼ represents a carbon-carbon single bond or no bond; wherein when the wavy line represents a carbon-carbon single bond, Z represents methylene and when the wavy line represents no bond, Z represents hydrogen or $C_2$–$C_4$ acyl for use in augmenting or enhancing perfume compositions, colognes and perfumed articles.

The structures of the compounds created as a result of carrying out the processes of U.S. Pat. Nos. 4,359,412 and 4,420,411 are different in kind rather than degree from the triisobutylene alcohols and esters of our invention particularly with respect to their actual chemical structures and their organoleptic properties.

The halogenated triisobutylene precursor materials used in the practice of our invention include compounds defined according to the generic structures:

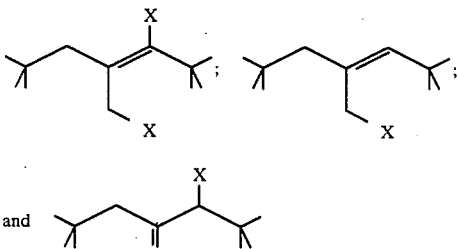

wherein X represents chloro or bromo. The prior art discloses halogenation of triisobutylene in U.S. Pat. No. 2,777,883 of Jan. 15, 1957 (incorporated herein by reference) and at Chemical Abstracts, Volume 66:45942n. The prior art does not infer that the resulting materials can be used to prepare corresponding esters or alcohols; nor does the prior art infer that the halogenated materials thus formed can be used to prepare any material useful in augmenting or enhancing the aroma of perfume compositions, colognes or perfumed articles.

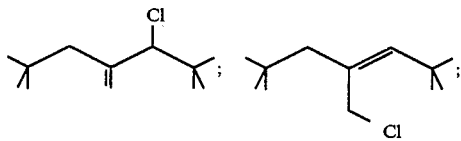

and 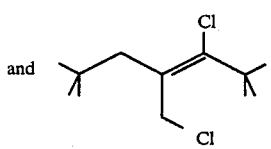

(Conditions: SE-30 column programmed at 150° C. isothermal).

Figure 1:
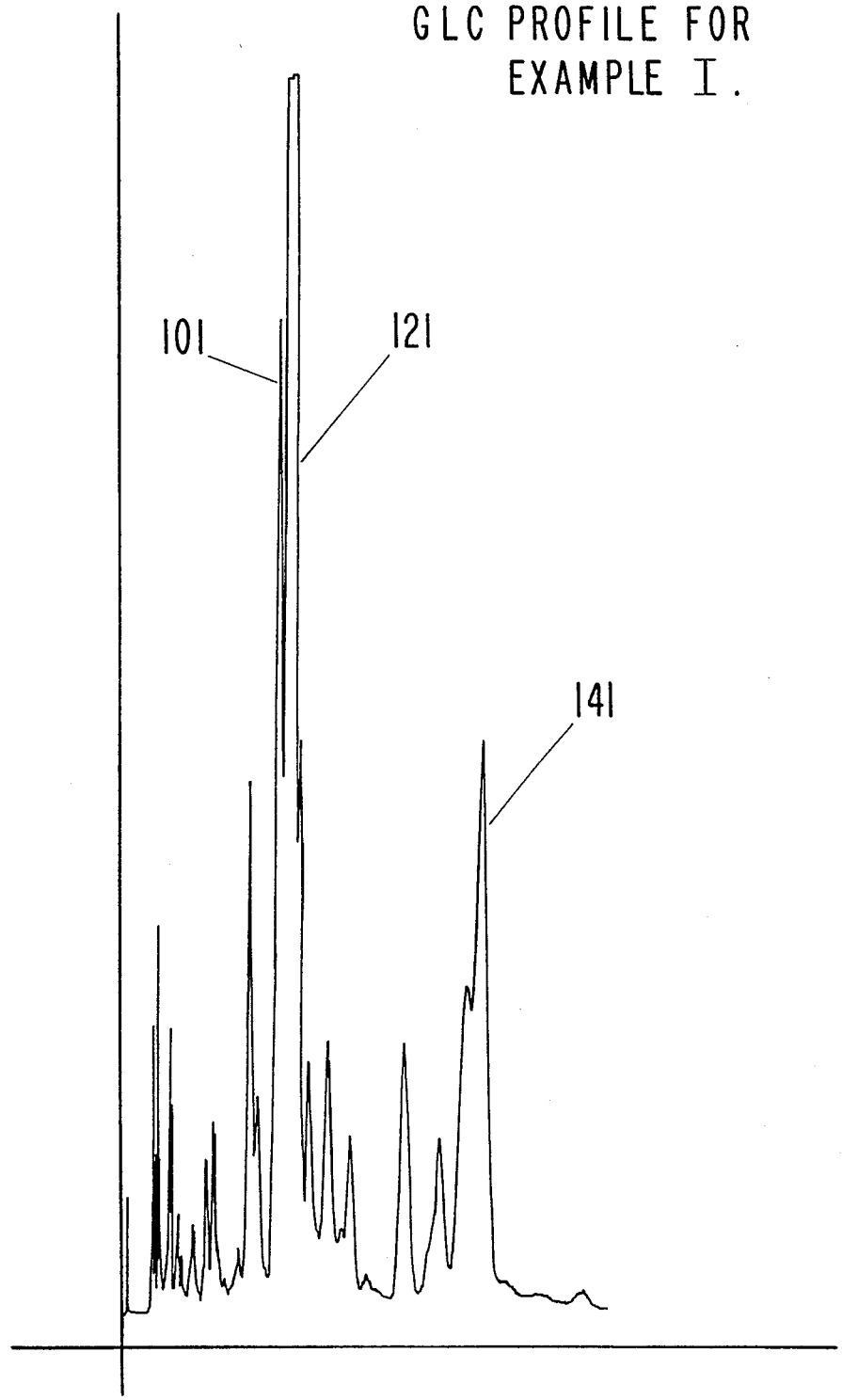
FIG. 1 is the GLC profile for the reaction product of Example I containing the compounds having the structures.
Figure 2:
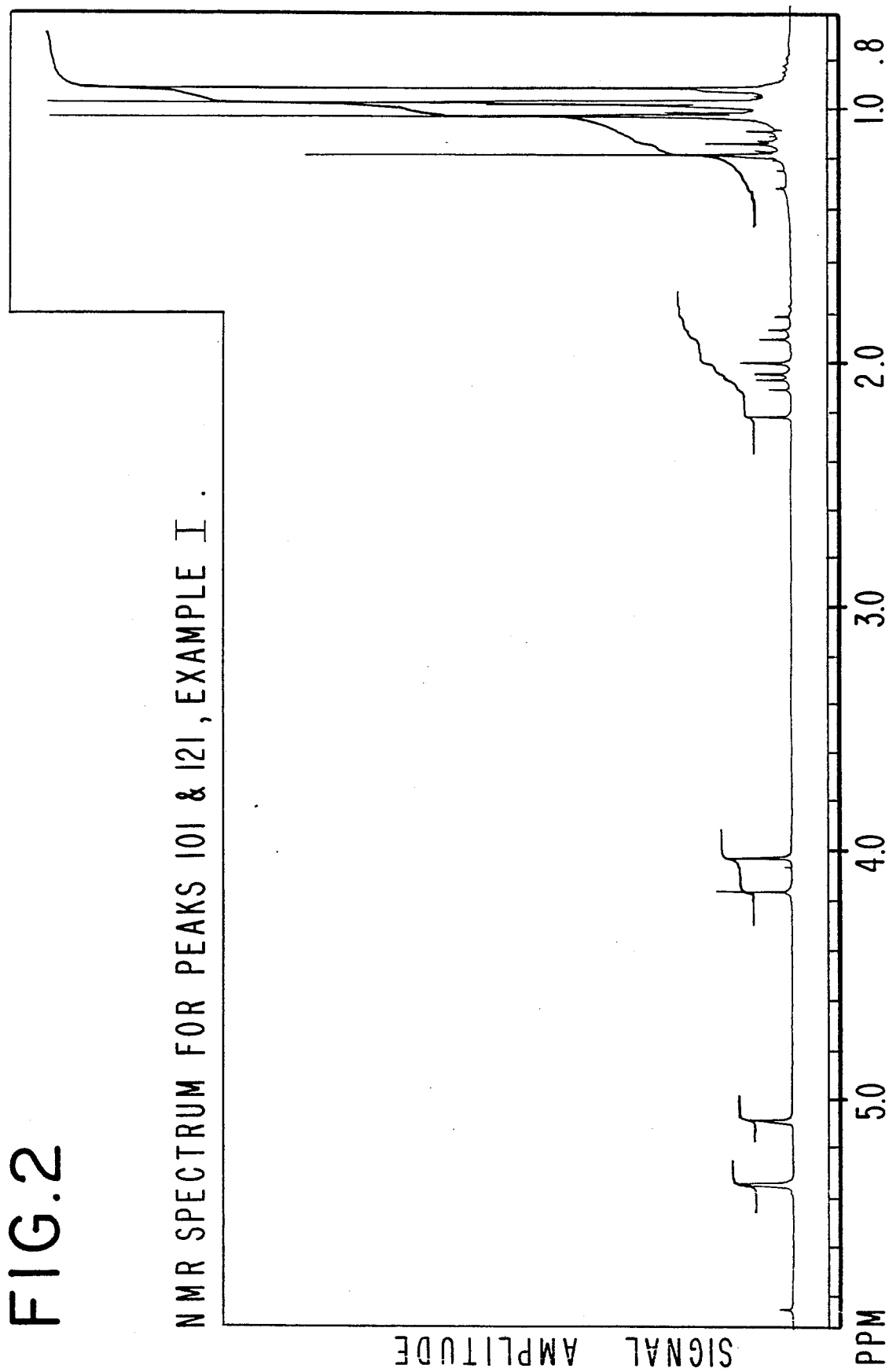

FIG. 2 is the NMR spectrum for the peaks indicated by reference numerals 101 and 121 on the GLC profile of FIG. 1; for the compounds having the structures:

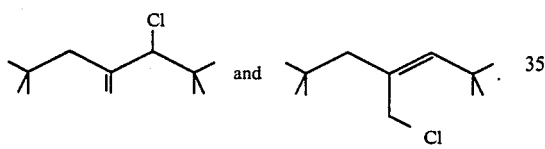

Figure 3:
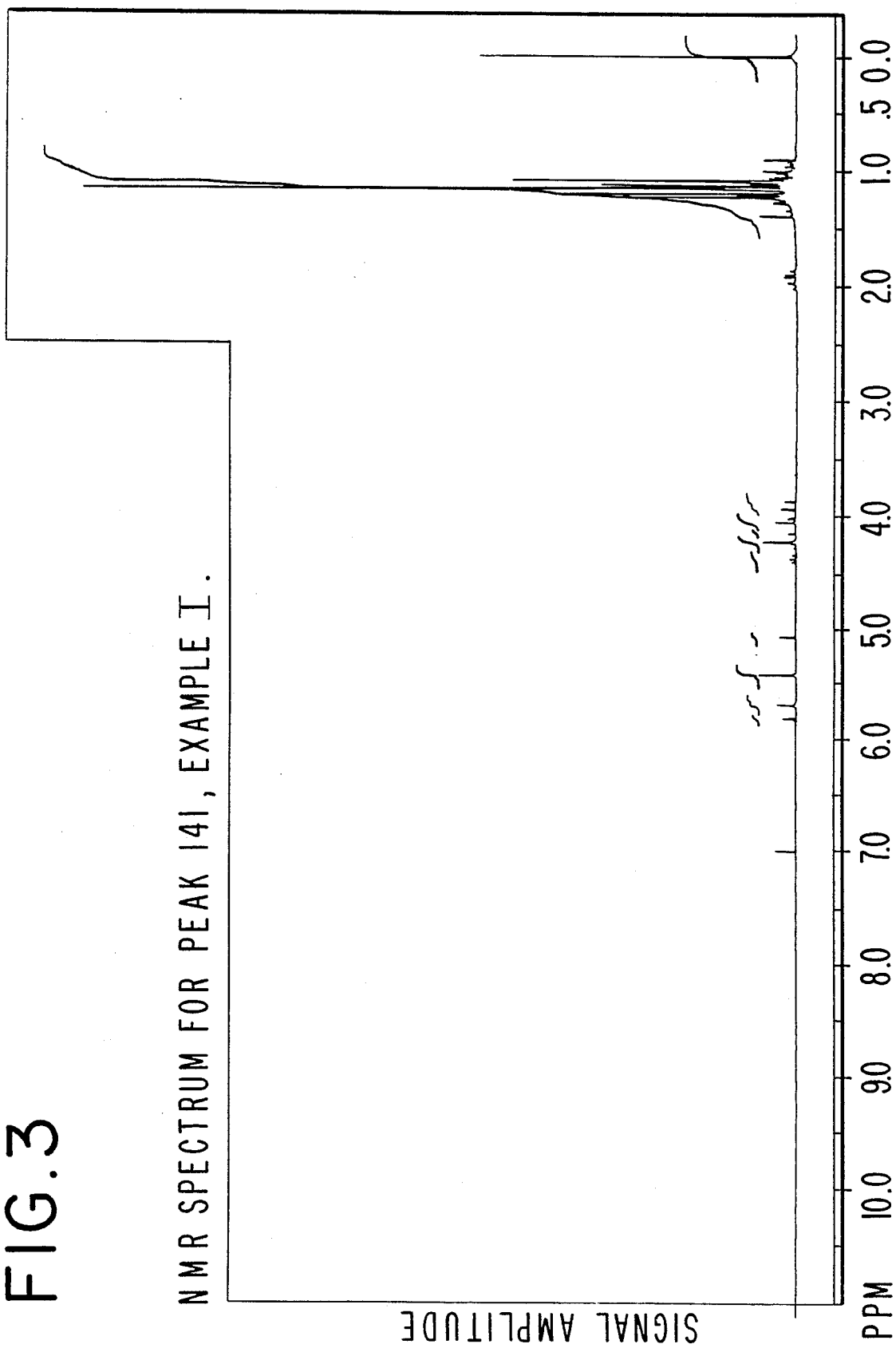

FIG. 3 is the NMR spectrum for the peak indicated by reference numeral 141 on the GLC profile of FIG. 1; for the compound having the structure:

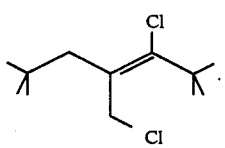

Figure 4:
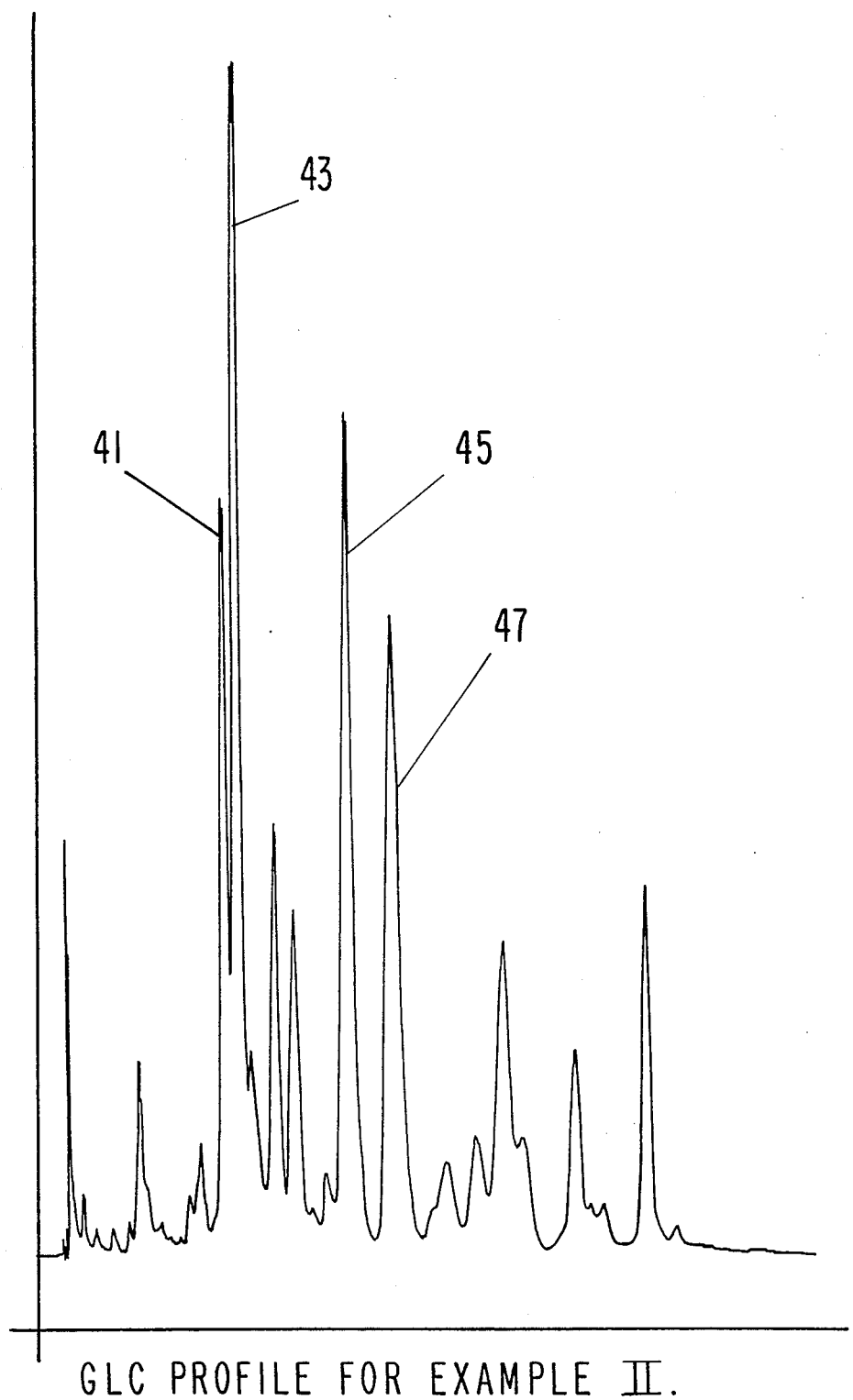

FIG. 4 is the GLC profile for the reaction product of Example II containing the compounds having the structures:

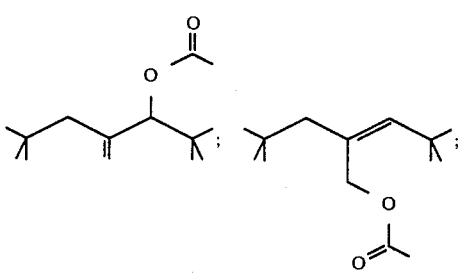

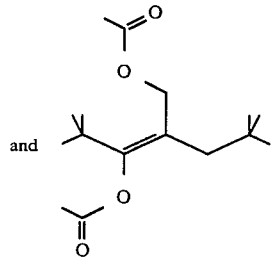

Figure 5:
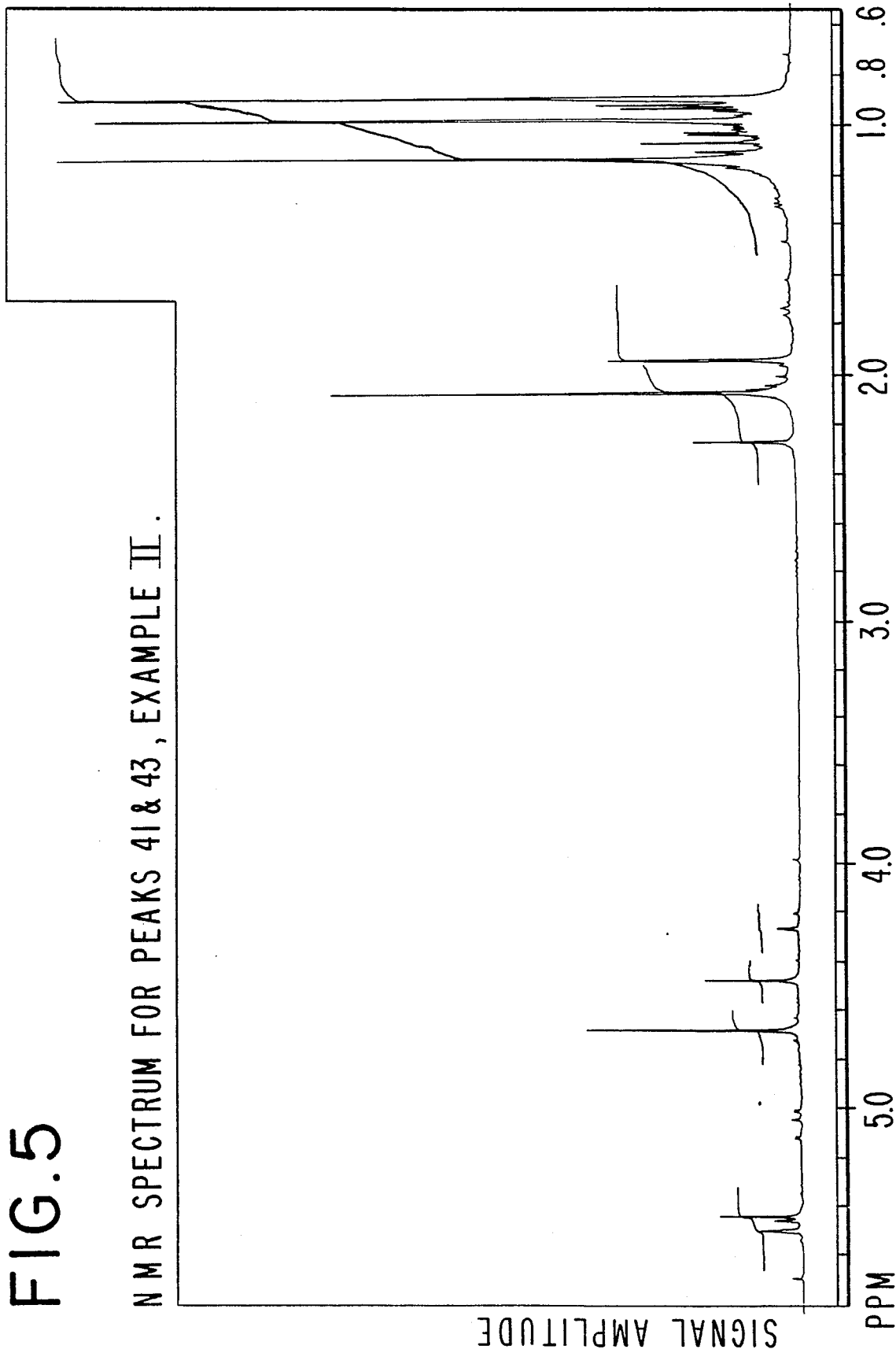

(Conditions: SE-30 column programmed at 150° C. isothermal). FIG. 5 is the NMR spectrum for the peaks indicated by reference numerals 41 and 43 on FIG. 4; for the compounds having the structures:

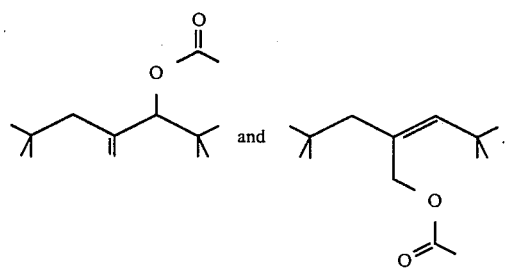

Figure 6:
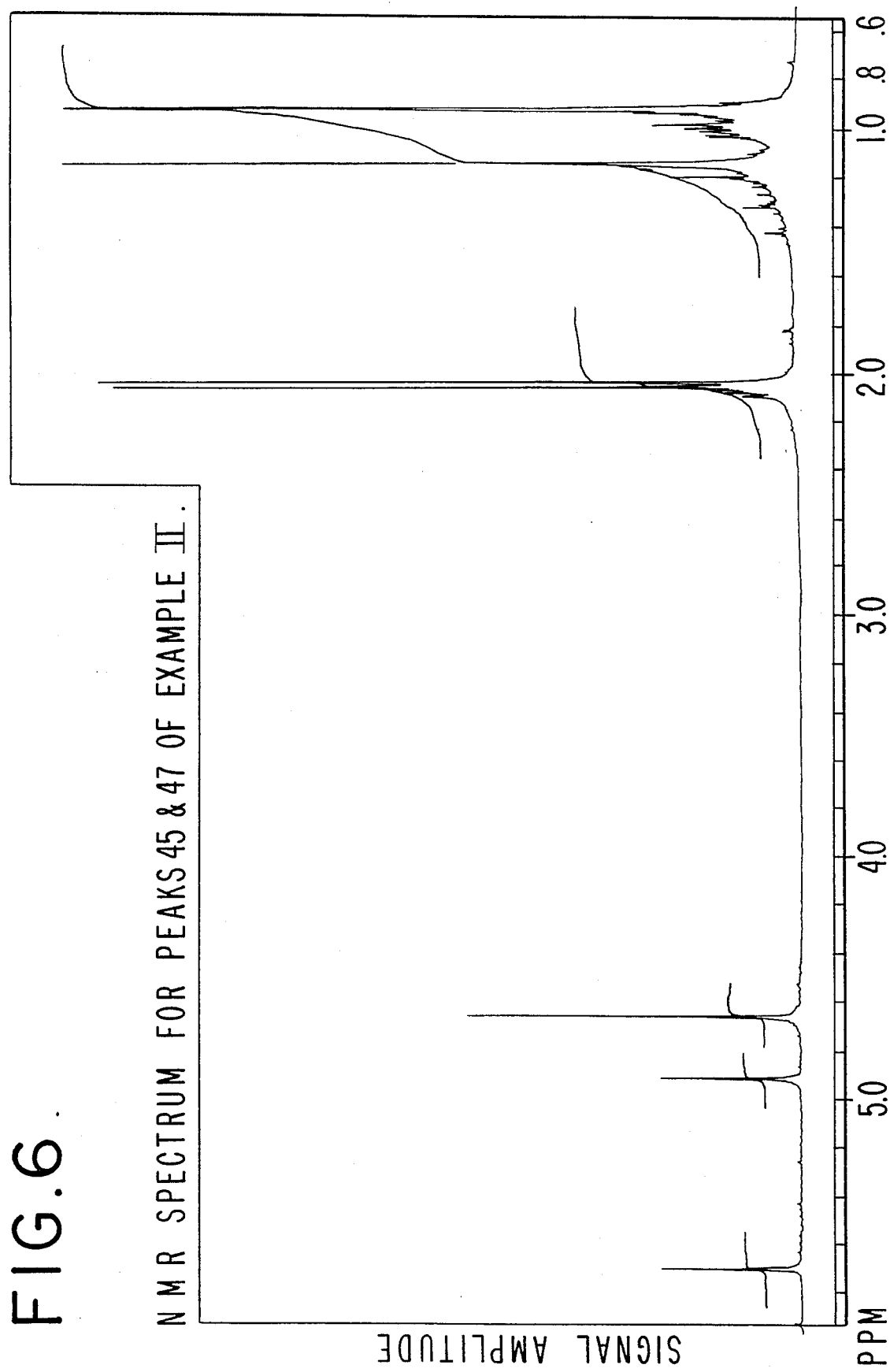

FIG. 6 is the NMR spectrum for the peaks indicated by reference numerals 45 and 47 on the GLC profile of FIG. 4; for the compound having the structure:

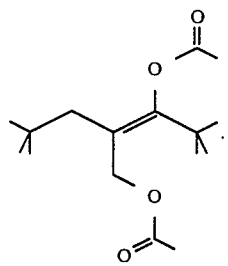

Figure 7:
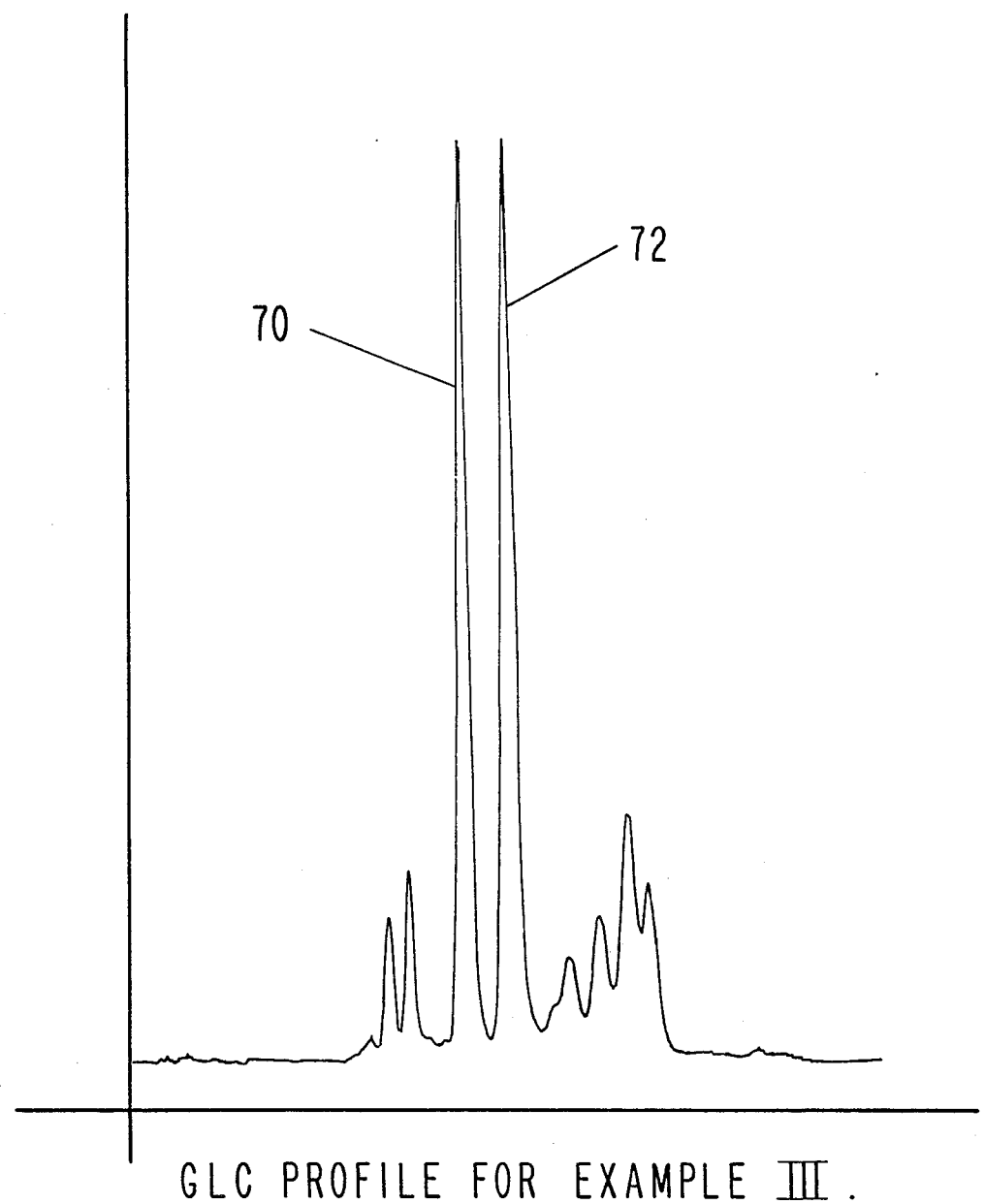

FIG. 7 is the GLC profile for the reaction product of Example III containing the compounds having the structures:

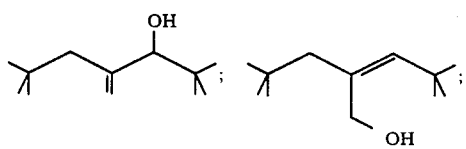

and 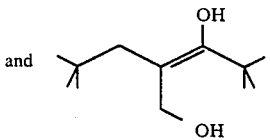

(Conditions: SE-30 column programmed at 150° C. isothermal).

Figure 8:
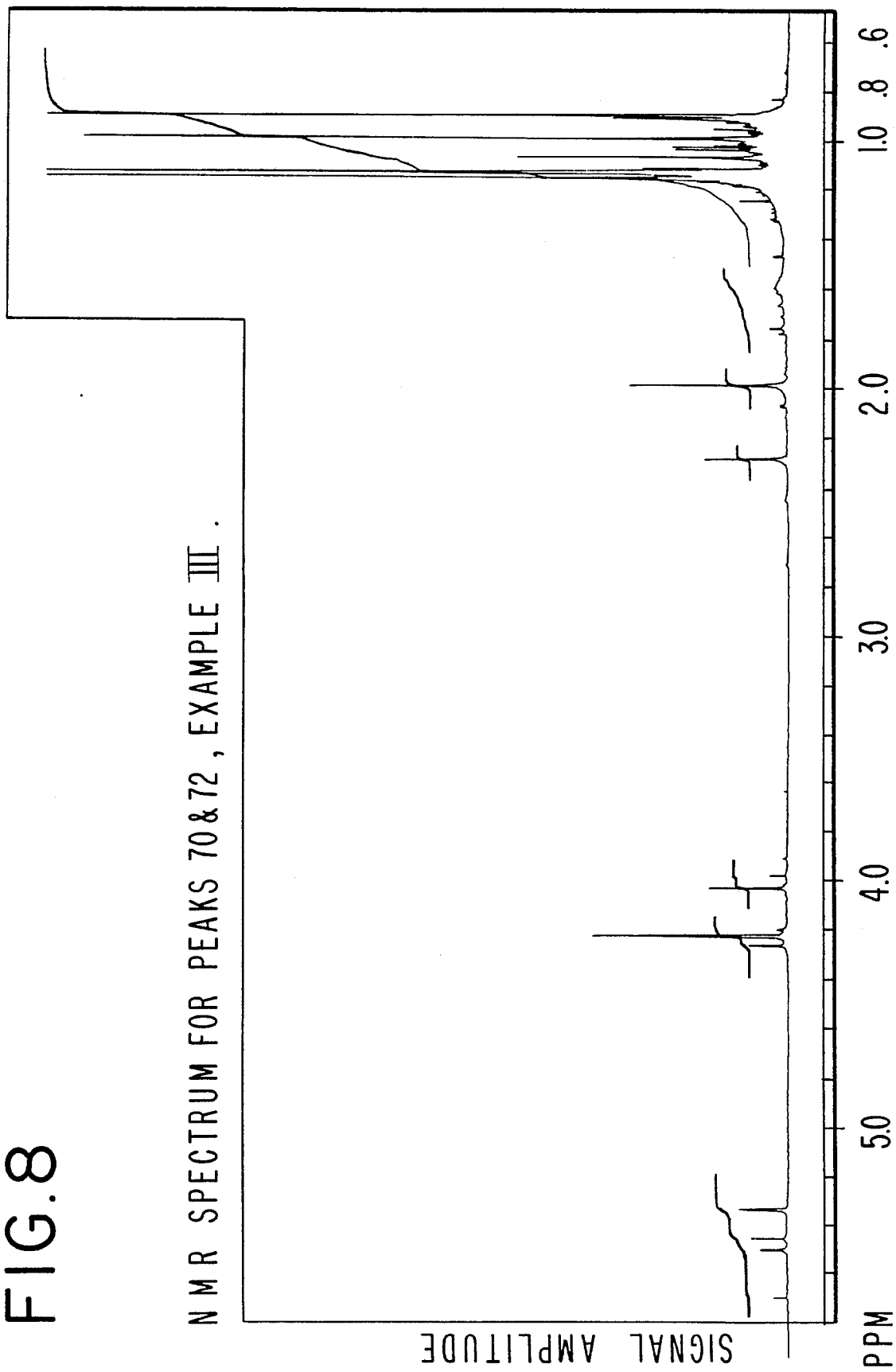

FIG. 8 is the NMR spectrum for the peaks indicated by reference numerals 70 and 72 on the GLC profile of FIG. 7; for the compounds having the structures:

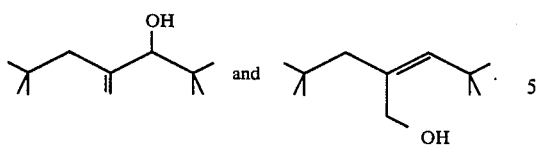

Figure 9:
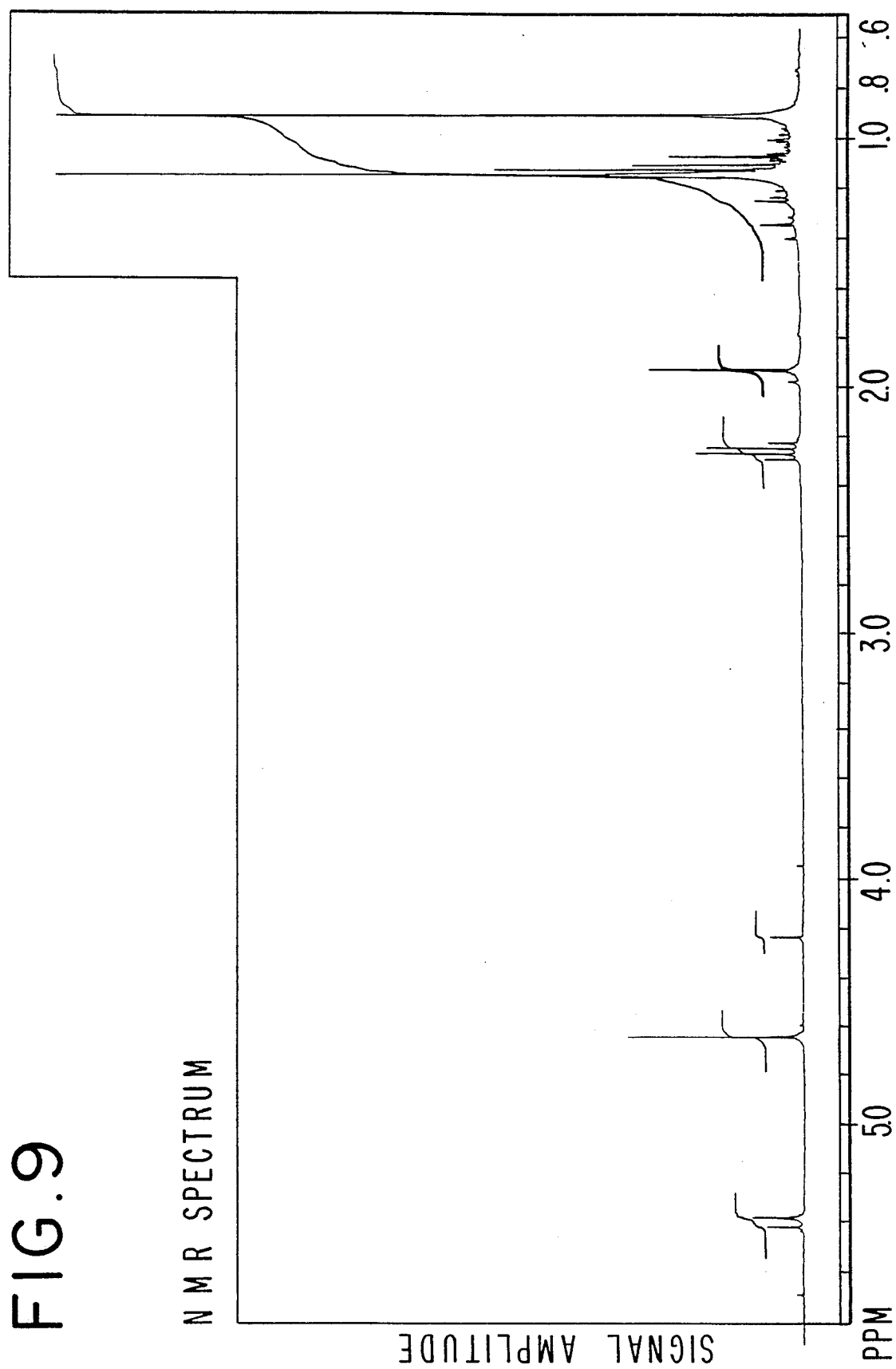

FIG. 9 is the NMR spectrum for the compound having the structure:

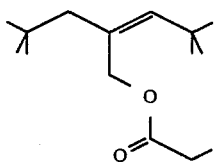

prepared according to Example IV.

Figure 10:
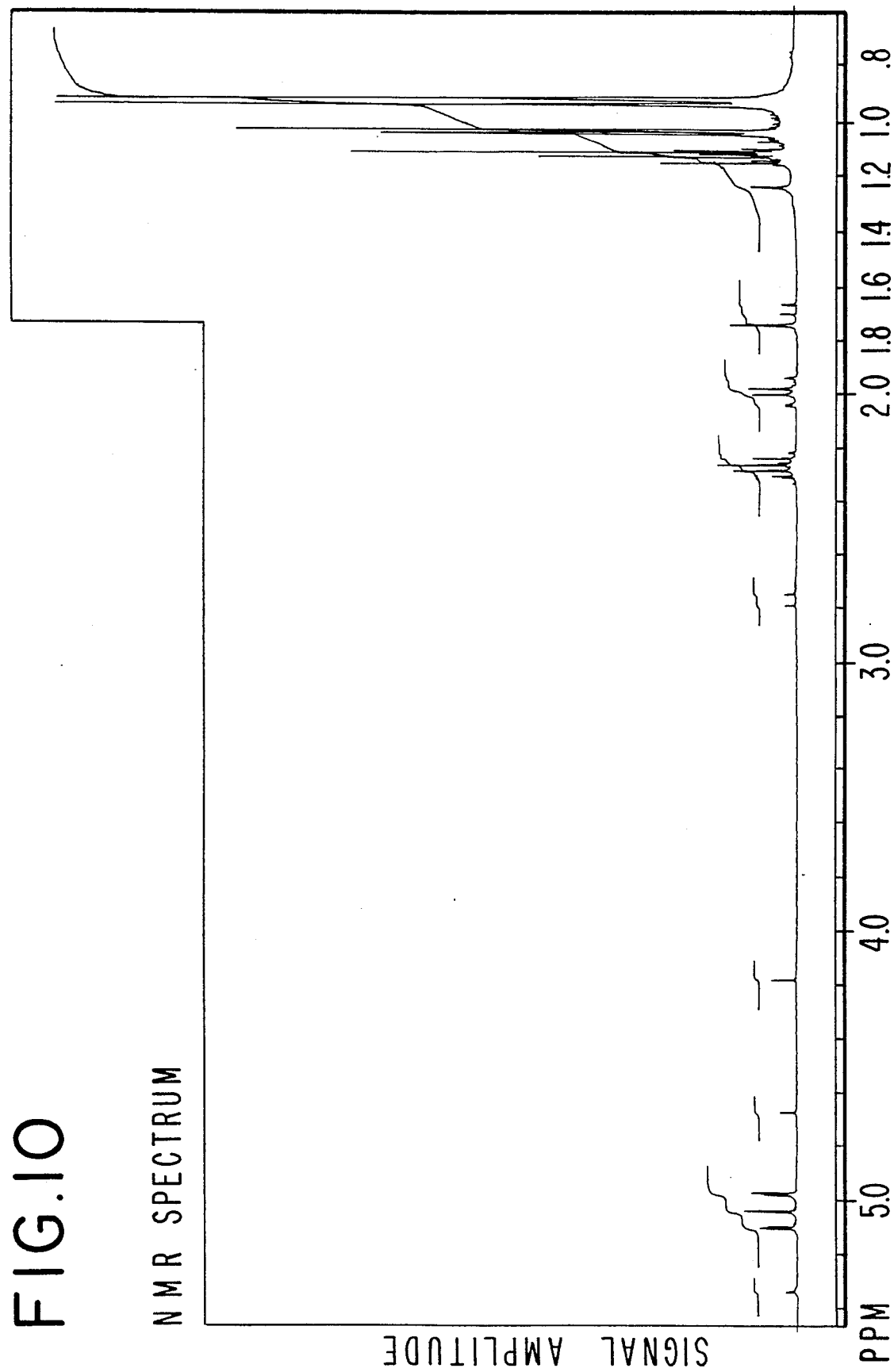

FIG. 10 is the NMR spectrum for the compound having the structure:

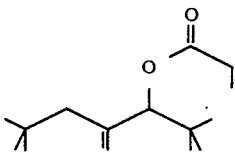

prepared according to Example IV.

Figures 11, 12:
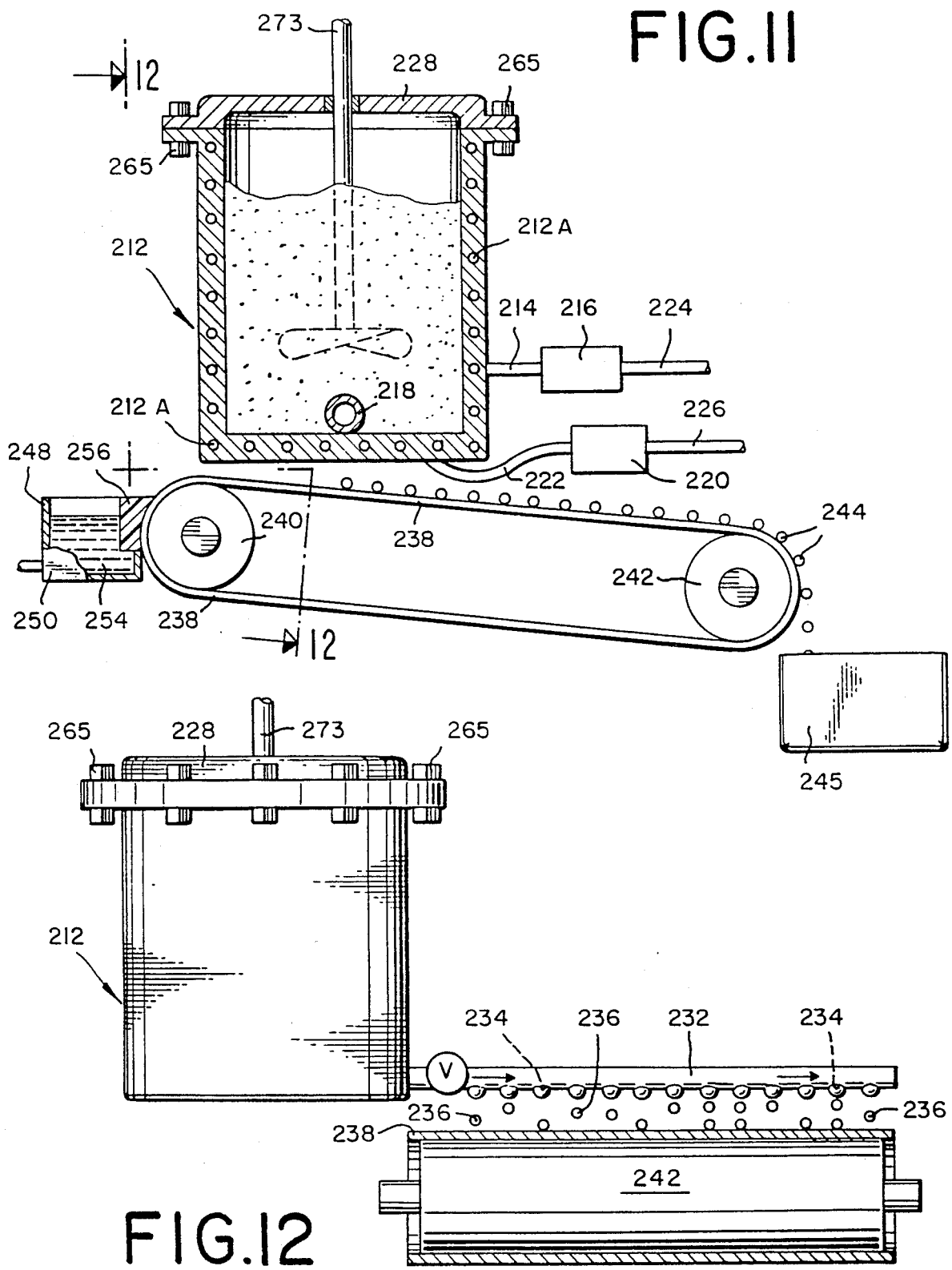

FIG. 11 represents a cut-away side elevation view of apparatus used in forming perfumed polymers which contain imbedded therein at least one of the triisobutylene alcohols and esters of our invention.

FIG. 12 is a front view of the apparatus of FIG. 11 looking in the direction of the arrows.

Figure 13:
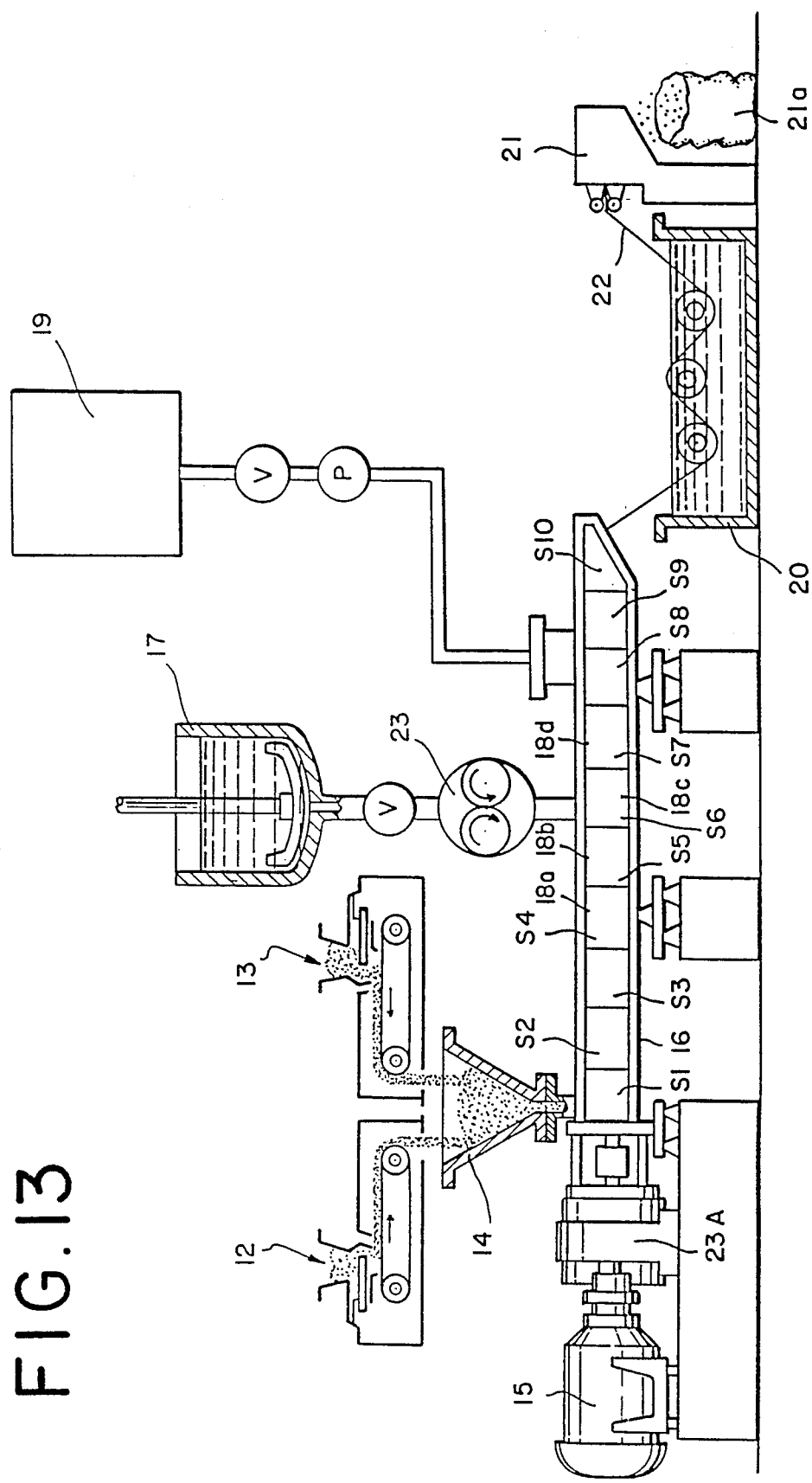

FIG. 13 is a cut-away side elevation schematic diagram of a screw extruder during the compounding of a resin with one of the triisobutylene alcohols and esters of our invention while simultaneously adding foaming agent into the hollow portion of the barrel of the extruder and incorporates the pelletizing apparatus used in pelletizing the extruded foamed tow produced as a result of the extrusion operation.

DETAILED DESCRIPTION OF THE DRAWINGS

FIG. 1 is the GLC profile for the reaction product of Example I. (Conditions: SE-30 column programmed at 150° C. isothermal).

The peaks indicated by reference numerals 101 and 121 are for the compounds having the structures:

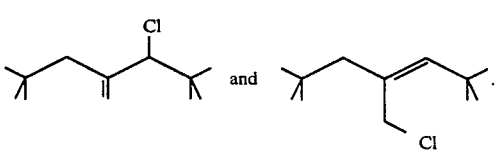

The peak indicated by reference numeral 141 is the peak for the compound having the structure:

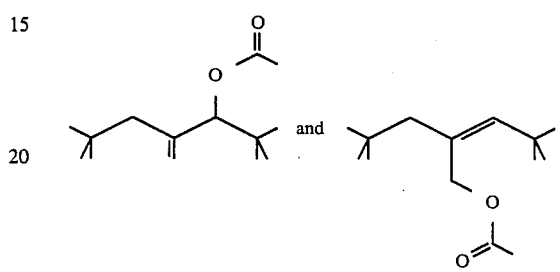

FIG. 4 is the GLC profile for the reaction product of Example II (Conditions: SE-30 column programmed at 150° C. isothermal). The peaks indicated by reference numerals 41 and 43 are for the compounds having the structures:

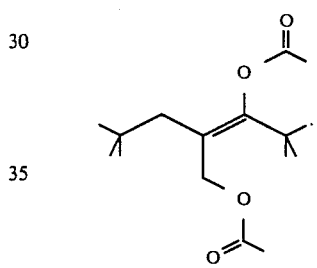

The peaks indicated by reference numerals 45 and 47 are for the compound having the structure:

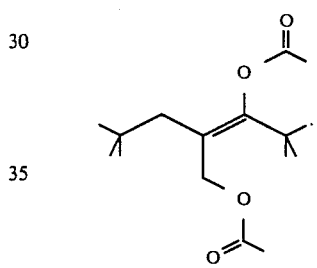

FIG. 7 is the GLC profile for the reaction product of Example III (Conditions: SE-30 column programmed at 150° C. isothermal).

The peaks indicated by reference numerals 70 and 72 are for the compounds having the structures:

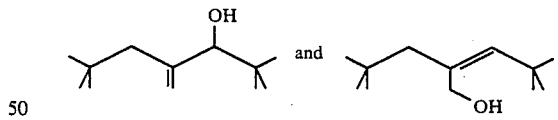

Referring to FIGS. 11 and 12, there is provided a process for forming scented polymer pellets (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. This process comprises heating the polymer or mixture of polymers to the melting point of said polymer or mixture of polymers, e.g., 250° C. in the case of low density polyethylene. The lower most portion of the container is maintained at a slightly lower temperature and the material in the container is taken off at such location for delivery through the conduit. Thus, referring to FIGS. 11 and 12, in particular, the apparatus used in producing such elements comprises a device for forming the polymer containing perfume, e.g., polyethylene or polyethylene-polyvinyl acetate or mixtures of same or polypropylene, which comprises a vat or container 212 into which the polymer taken alone or in admixture with other copolymers and the perfuming substance which is at least one of the triisobutylene alcohols and esters of our invention and other compatible perfumes is placed. The container is closed by means of an air-tight lid 228 and clamped to the container by bolts 265. A stirrer 273 traverses the lid or cover 228 in an air-tight manner and is rotatable in a suitable manner. A surrounding cylinder 212A having heating coils which are supplied with electric current through cable 214 from a rheostat or control 216 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 connected thereto through a connecting wire 222 to maintain the lower portion of the container 212 within a temperature range of 220°–270° C.

Thus, the polymer or mixture of polymers added to the container 212 is heated from 10–12 hours, whereafter the perfume composition or perfume material which contains one or more of the triisobutylene alcohols and esters of our invention is quickly added to the melt. Generally, about 10–45 percent by weight of the resulting mixture of the perfumery substance is added to the polymer.

After the perfume material containing at least one of the triisobutylene alcohols and esters of our invention is added to the container 212 the mixture is stirred for a few minutes, for example, 5–15 minutes and maintained within the temperature ranges indicated previously by the heating coil 212A. The controls 216 and 220 are connected through cells 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with one or more of the triisobutylene alcohols and esters of our invention or mixture of perfume substance and one or more of the triisobutylene alcohols and esters of our invention, will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dropping or dripping of molten polymer intimately admixed with the perfume substance which is all or which contains one or more of the triisobutylene alcohols and esters of our invention through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water or another suitable cooling liquid to insure the rapid cooling of each of the pellets 244. The pellets 244 are then collected from the container 250 and utilized for the formation of other functional products, e.g., garbage bags and the like.

Referring to FIG. 13, FIG. 13 is a schematic cut-away elevation diagram of the extrusion and pelletizing apparatus useful in carrying out a process for incorporation of at least one of the triisobutylene alcohols and esters of our invention into polymers during the operation of said apparatus. Motor 15 drives the extruder screws located at 23A in barrel 16, the extruder being operated at temperatures in the range of about 150° C. up to about 250° C. At the beginning of the barrel resin at source 12 together with additives, e.g., opacifiers, processing aids, colors, pearlescent agents and densifiers at location 13 is added via addition funnel 14 into the extruder. Simultaneously (when the operation reaches "steady state",) one or more of the triisobutylene alcohols and esters of our invention is added to the extruder at one, two or more of barrel segments 3–8 of the extruder (which may be a twin screw or single screw extruder) at locations 18a, 18b, 18c and 18d by means of gear pump 23 from source 17. From source 19 into barrel segments 5–10, the gaseous or liquid blowing agents, e.g., nitrogen, carbon dioxide and the like are added simultaneously with the addition of at least one of the triisobutylene alcohols and esters of our invention. The feed rate range of the resin is about 80–300 pounds per hour. The feed rate range of at least one of the triisobutylene alcohols and esters taken alone or further together with other perfumant is between 1 and 45% of the feed rate range of the resin. The blowing agent rate range is such that the pressure of the gas or the pressure over the liquid being fed into the extruder is between about 50 and 2000 psig. If desired, the extruded ribbon or cylinder may be passed through water bath 20 and pelletizer 21 into collection apparatus 21a.

THE INVENTION

Our invention provides triisobutylene alcohols and esters defined according to the generic structure:

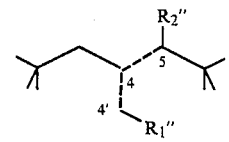

wherein one of the dashed lines is a carbon-carbon double bond and the other of the dashed lines is a carbon-carbon single bond; wherein $R_1''$ and $R_2''$ are the same or different and each represents hydrogen, hydroxyl or $C_1$–$C_3$ acyloxy and composition containing such triisobutylene alcohols and esters produced according to the process of reacting a halogen with triisobutylene according to the reaction:

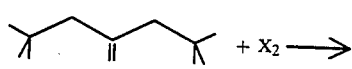

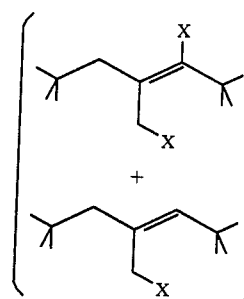

and then reacting the resulting halogenated triisobutylene with a metal acylate having the structure:

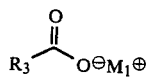

according to the reaction:

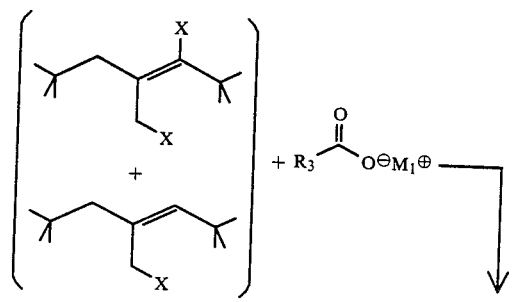

and then, if desired, hydrolyzing the resulting esters with base according to the reaction:

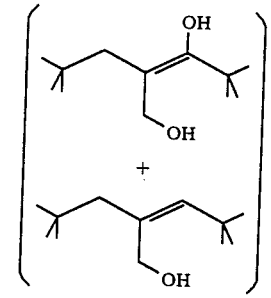

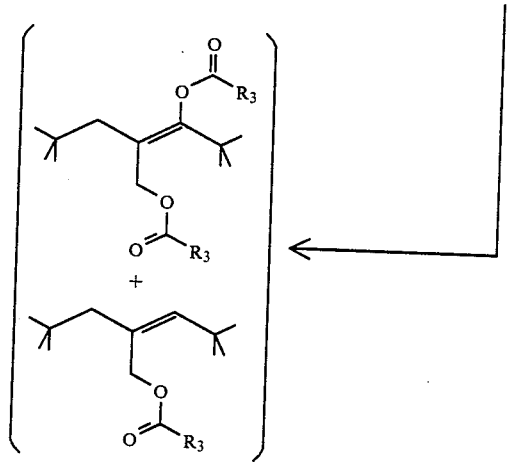

wherein $R_3$ represents hydrogen or $C_1$ or $C_2$ alkyl; wherein $M_1$ represents sodium or potassium; wherein $M_2$ represents sodium or potassium; and wherein X represents chloro or bromo; and uses thereof in augmenting or enhancing the aroma of perfume compositions, colognes or perfumed articles including but not limited to solid or liquid anionic, cationic, nonionic or zwitterionic detergents; fabric softeners; drier-added fabric softener articles; hair preparations and cosmetic powders.

In carrying out the halogenation reaction, to wit:

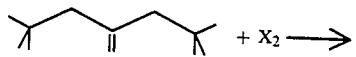

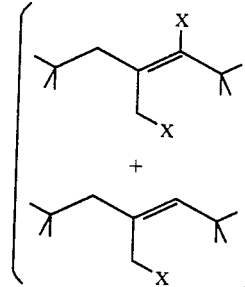

the reaction takes place at a temperature in the range of from about 0° C. up to about 50° C. in the presence of or in the absence of a solvent. When a solvent is used the solvent may be a hydrocarbon or a chlorocarbon solvent. The reaction is carried out in a base such as sodium bicarbonate or potassium carbonate or a mixture of sodium bicarbonate, potassium carbonate and trialkyl amines (preferably). The number of equivalents of base needed in this reaction is from about 0.5 up to about 1.5 equivalence. The resulting mixture contains compounds having the structures:

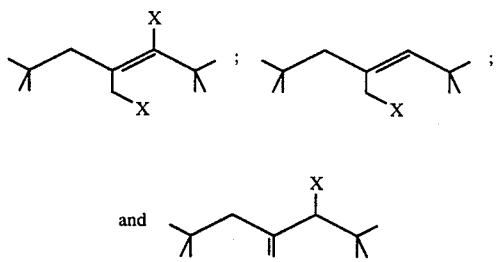

and X may be chloro or bromo; preferably chloro.

In carrying out the reaction, to wit:

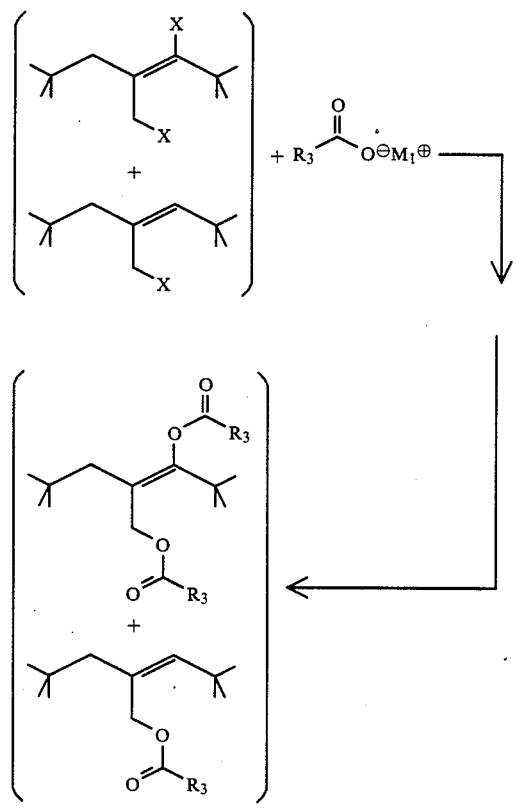

wherein $R_3$ is hydrogen or $C_1$ or $C_2$ alkyl and $M_1$ is sodium or potassium, the reaction is carried out under anhydrous conditions at a temperature in the range of from about 100° C. up to about 180° C.; in the absence of solvent or in the presence of a high boiling solvent.

In carrying out the reaction:

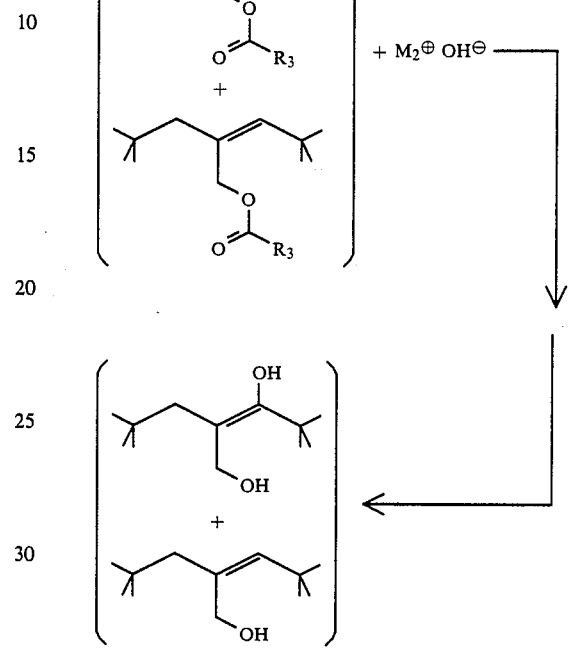

wherein $M_2$ represents sodium or potassium, this reaction is carried out under standard hydrolysis conditions preferably with an alcoholic cosolvent at temperatures in the range of from about 70° up to about 100° C.; more preferably at reflux conditions.

The following table sets forth structures of compounds contained in reaction products and the organoleptic properties of such reaction products:

TABLE I

| Structures of Triisobutylene Alcohols and Esters In Mixtures: | Perfumery Properties |
|---|---|
| Mixture of compounds having the structures: | A myrrh-like, olibanum-like, balsamic, peppery, fruity, and smokey aroma with myrrh, olibanum, honey-like, fruity, ozoney and leathery topnotes. |

TABLE I-continued

| Structures of Triisobutylene Alcohols and Esters In Mixtures: | Perfumery Properties |
|---|---|
| 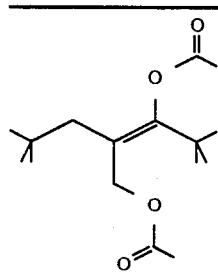<br>prepared according to Example II, bulked distillation fractions 10–17. | |
| Mixture of compounds having the structures:<br>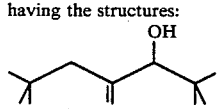<br>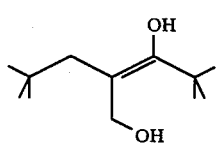<br>and<br>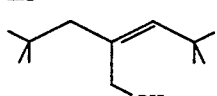<br>prepared according to Example III, bulked distillation fractions 5–12. | A rose, geranium, peppery, herbaceous and fruity aroma profile with fresh, peppery, rose, geranium, minty, fruity and green topnotes. |
| Mixture of compounds having the structures:<br>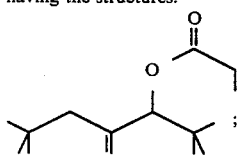<br>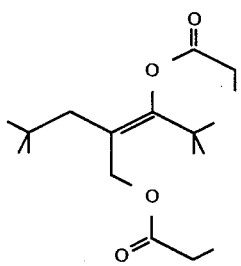<br>and<br>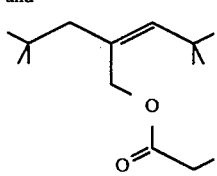<br>prepared according to Example IV, fraction 11. | An olibanum resin-like, myrrh-like, woody, linseed oil-like aroma profile with leathery undertones. |

One or more triisobutylene alcohols and esters prepared in accordance with the process of our invention and one or more auxiliary perfume ingredients including, for example, alcohols (other than the triisobutylene alcohols and esters of our invention), aldehydes, ketones, terpinic hydrocarbons, nitriles, esters (other than the triisobutylene alcohols and esters of our invention), lactones, natural essential oils and synthetic essential oils may be admixed so that the combined odors of the individual components produce a pleasant and desired fragrance, particularly, and preferably, in the floral, herbaceous and leathery fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh-smelling materials.

In perfume compositions, it is the individual components which contribute to their particular olfactory characteristics, however, the over-all sensory effect of the perfume composition will be at least the sum total of the effects of each of the ingredients. Thus, the triisobutylene alcohols and esters of our invention can be used to alter, modify or enhance the aroma characteristics of a perfume composition, for example, by utilizing or moderating the olfactory reaction contributed by another ingredient in the composition.

The amount of one or more of the triisobutylene alcohols and esters of our invention prepared in accordance with the process of our invention which will be effective in perfume compositions as well as in perfumed articles (e.g., anionic, cationic, nonionic and zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.01% of at least one of the triisobutylene alcohols and esters of our invention and less than 50% of at least one of the triisobutylene alcohols and esters of our invention or even less, e.g., 0.005%) can be used to impart myrrh-like, olibanum-like, balsamic, peppery, fruity, rose, geranium, herbaceous, woody and linseed oil-like aromas, with myrrh, olibanum, honey-like, fruity, ozoney, leathery, fresh peppery, rose, geranium, minty and green topnotes and leathery undertones to solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

One or more of the triisobutylene alcohols and esters of our invention are useful (taken alone or together with other ingredients in perfume compositions) as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders, and perfumed polymers and articles of manufacture produced from said perfumed polymers. When used as (an) olfactory component(s) as little as 0.2% of at least one of the triisobutylene alcohols and esters prepared in accordance with the process of our invention will suffice to impart an intense myrrh-like, olibanum-like, balsamic, peppery, fruity, rose, geranium, herbaceous, woody and linseed oil-like aroma, with myrrh, olibanum, honey-like, fruity, ozoney, leathery, fresh, peppery, rose, geranium, minty and green topnotes and leathery undertones to floral, woody and leathery formulations. Generally, no more than 6% of one or more of the triisobutylene alcohols and esters of our invention based on the ultimate end product is required in the perfumed article composition. Accordingly, the range of one or more of the triisobutylene alcohols and esters in the perfumed articles is from about 0.2% by weight of the triisobutylene alcohols and esters up to about 6% by weight based on the perfumed article. In addition, the perfume composition or fragrance composition of our invention can contain a vehicle or carrier for one or more of the triisobutylene alcohols and esters of our invention. The vehicle can be a liquid such as a non-toxic alcohol, e.g., ethyl alcohol, a non-toxic glycol, e.g., propylene glycol or the like. The carrier can also be an absorbent solid, such as a gum (e.g., gum arabic, guar gum or xanthan gum) or components for encapsulating the composition (such as gelatin) as by coacervation; or such as a urea-formaldehyde prepolymer forming a capsule shell around a liquid perfumed center).

Our invention also relates to the utilization of controlled release technology for the controlled release of perfumes into gaseous environments from polymers such as mixtures of epsilon polycaprolactone polymers and polyethylene which polyepsilon caprolactone polymers are defined according to at least one of the structures:

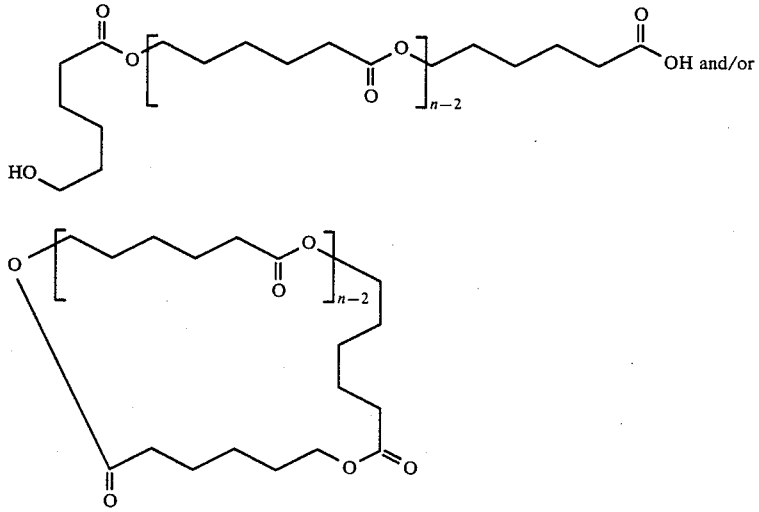

wherein "n" is from about 50 up to about 1,200 with the proviso that the average "n" in the system varies from about 150 up to about 700 according to the mathematical statement:

[700 ≧ n ≧ 150]

with the term n being the average number of repeating monomeric units for the epsilon polycaprolactone polymer. The perfumed material's release rate from such polymer mixture is close to "zero order". As a general rule, the release rate in a polymeric matrix is proportional to $t^{-\frac{1}{2}}$ until about 60% of the functional fluid is released from the polymeric matrix. The release rate thereafter is related exponentially to time as a general rule according to the equation:

$$\frac{dM_t}{dt} = k_1 e^{-k_2 t}$$

wherein $k_1$ and $k_2$ are constants. According to Kydonieus, "Controlled Release Technologies: Methods, Theory, and Applications" (cited, supra, the amount of perfume composition released is proportional to time as long as the concentration of perfume material present, e.g., one or more of the triisobutylene alcohols and esters of our invention is higher than the solubility of the agent in the matrix. Thus, such dispersed systems are similar to the dissolved systems except that instead of a decreased release rate after 60% of the perfume material has been emitted, the relationship holds almost over the complete release curve. Kydonieus further states, that if one assumes that the release of functional fluid by diffusion is negligible in monolithic erodible systems, the speed of erosion will control the release rate and release by erosion by a surface-area-depending phenomenon, the release constant (zero order) as long as the surface area does not change during the erosion period. This is the case with the polymers containing one or more of the triisobutylene alcohols and esters of our invention.

The polyepsilon caprolactone polymers useful in practicing our invention are more specifically described in the brochure of the Union Carbide Corporation, 270 Park Avenue, N.Y., N.Y. 10017, entitled "NEW POLYCAPROLACTONE TERMOPLASTIC POLYMERS PCL-300 and PCL-700". These polyepsilon caprolactone polymers are composed of a repeating sequence of non-polar methylene groups and relatively polar ester groups. The average number of repeating monomeric units varies between 150 and 700 depending on the particular "PCL" number. Thus, regarding PCL-300 the average number of repeating monomeric units is about 300. Regarding PCL-700, the average number of repeating monomeric units is 700.

The polyepsilon caprolactone homopolymers which are ultimately taken in admixture with such materials as polyethylene useful in the practice of our invention may also be stabilized using stabilizers as defined in U.S. Pat. No. 4,360,682 issued on Nov. 23, 1982, the specification for which is incorporated herein by reference. The stabilizing material which stabilizes the polyepsilon caprolactone useful in conjunction with our invention against discoloration are dihy-droxybenzenes such as hydroquinone or compounds having the formula:

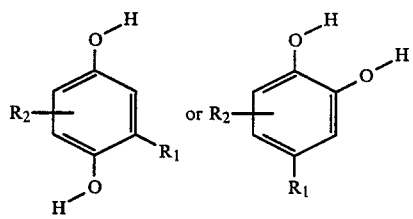

in which $R_1$ is alkyl of from 1 to 8 carbon atoms, and $R_2$ is hydrogen or alkyl of 1 to 8 carbon atoms. It is preferable to have such stabilizer in the polyepsilon caprolactone homopolymer in an amount of from about 100 to 500 ppm. Such stabilizers do not interfer with the functional fluids dissolved and/or adsorbed into the polymeric matrix.

The method of incorporating one or more of the triisobutylene alcohols and esters of our invention or perfume compositions containing same into the polymers may be according to the technique of U.S. Pat. No. 3,505,432 issued on Apr. 7, 1970 (the specification for which is incorporated by reference herein) or U.S. Pat. No. 4,247,498 issued on Jan. 27, 1981, the disclosure of which is incorporated by reference herein.

Thus, for example, a first amount of liquid polyethylene-polyepsion caprolactone polymer mixture (50:50) is mixed with one or more of the triisobutylene alcohols and esters of our invention. Drops are formed from the mixture and the drops are solidified. The solidified drops are then melted, if desired, with a second amount of unscented low density polyethylene, for example, or polypropylene, for example. Usually, but not necessarily, the second amount of polymer is larger than the first amount. The resulting mixture thus obtained is solidified subsequent to or prior to ultimate casting into a utilitarian shape.

Thus, in accordance with one aspect of our invention the imparting of scent is effected in two stages. In a first stage, a 50:50 (weight:weight) polyepsilon caprolactone, e.g., PCL-700:polyethylene in molten form is admixed with a high percentage of one of the triisobutylene alcohols and esters of our invention and the mixture is solidified in the form of pellets or beads. These pellets or beads thus contain a high percentage of one or more of the triisobutylene alcohols and esters (e.g., up to 45% by weight of the entire mixture) and may be used as "master pellets" which thereafter, in a second stage, if desired, may be admixed and liquified with additional polymers such as additional polyethylene or mixtures of polyethylene and polyepsilon caprolactone in an unscented state, or unscented polypropylene. In addition, additional polymers or copolymers may be used, for example, copolymers specified and described in United Kingdom Patent Specification No. 1,589,201 published on May 7, 1981, the specification for which is incorporated by reference herein.

In accordance with the present invention at least one or more of the triisobutylene alcohols and esters of our invention is added to the polymer in a large closed container or drum which is maintained under controlled temperature conditions while the polymer in a melted condition is mixed with at least one or more of the triisobutylene alcohols and esters under agitation.

In order that the perfume be added uniformly to the polymer, the temperature of the melt is constantly controlled during the process. The polymer-perfume mixture is then directed through an elongated conduit or pipe element having a plurality of orifices adjacent to the lower most portion thereof. The polymer enriched by at least one or more of the triisobutylene alcohols and esters of our invention is permitted to drip through the orifices onto a continuously moving, cooled conveyor upon which the polymer containing at least one or more of the triisobutylene alcohols and esters of our invention solidifies into small size pellets with the perfume imprisoned therein. The apparatus useful in conjunction with this process advantageously includes a conveyor of a material which will not adhere to the polymer which contains at least one or more of the triisobutylene alcohols and esters of our invention.

In order that the droplets form into uniform pellets or beads, the conveyor is continuously washed with a liquid such as water to maintain the surface relatively cool. The pellets are delivered by the conveyor into a container and packaged for shipment.

The following Examples I-IV serve to illustrate processes for preparing the triisobutylene alcohols and esters of our invention. The examples following Example IV are illustrative of the organoleptic utilities of the triisobutylene alcohols and esters of our invention. All parts and percentages given herein are by weight unless otherwise specified.

EXAMPLE I

Chlorination of Triisobutylene

Reaction:

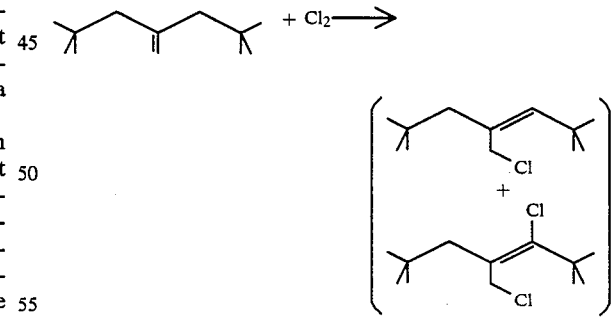

(and in addition, the compound having the structure:

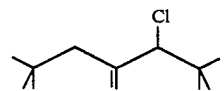

is formed).

Into a 10 liter reaction vessel is placed 4200 grams of triisobutylene and 2520 grams of sodium bicarbonate. The resulting mixture is heated to 35° C. Over a five hour period, chlorine gas is fed into the reaction mass with stirring while maintaining the temperature at 35°–40° C.

At the end of the five hour period, the reaction mass is quenched into 6 liters of water and washed with a 10% salt-water mixture.

FIG. 1 is the GLC profile of the reaction product (Conditions: SE-30 column programmed at 150° C. isothermal). The peaks indicated by reference numerals 101 and 121 are the peaks for the compounds having the structures:

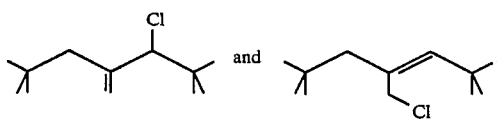

The peak indicated by reference numeral 141 is the peak for the compound having the structure:

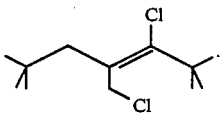

FIG. 2 is the NMR spectrum for the compounds having the structures:

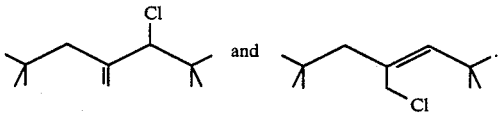

FIG. 3 is the NMR spectrum for the compound having the structure:

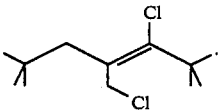

EXAMPLE II

Preparation of Triisobutylene Acetate Composition

Reaction:

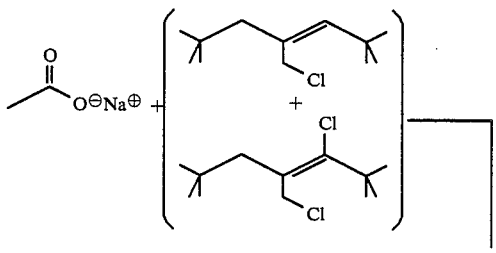

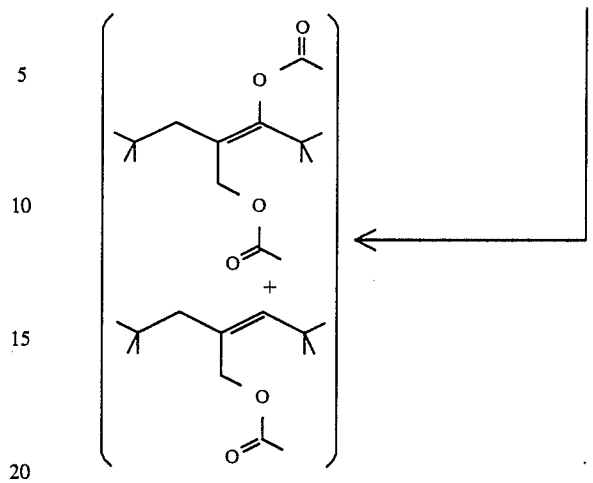

(and in addition, the compound having the structure:

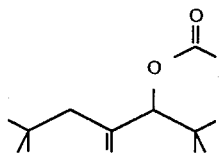

is prepared in the mixture).

Into a 5 liter reaction vessel is placed 820 grams of sodium acetate and 1800 grams of acetic acid. The mixture, with stirring is heated to a 100° C. While maintaining the temperature at 100° C. over a period of one hour, 1500 grams of the triisobutylene chloride prepared according to Example I is added to the reaction mass. At the end of the one hour period, the temperature is raised to 120° C. at reflux and maintained at reflux for a period of two hours. At the end of the two hour period, acetic acid is removed from the reaction mass using a Bidwell apparatus, the pot temperature being 150°–155° C. The temperature is maintained at 155° C. for a period of six hours. At the end of the six hour period, the reaction mass is cooled to 80° C. and 2 liters of water is added thereto. The reaction mass is then washed (to neutral) with sodium carbonate. The reaction mass is then distilled yielding the following fractions:

| Fraction No. | Vapor Temp. (°C.) | Liquid Temp. (°C.) | Vacuum mm/Hg. Pressure |
|---|---|---|---|
| 1 | 23/95 | 23/105 | 10/8 |
| 2 | 90 | 110 | 6.0 |
| 3 | 90 | 112 | 6.0 |
| 4 | 92 | 115 | 6.0 |
| 5 | 92 | 116 | 6.0 |
| 6 | 96 | 118 | 6.0 |
| 7 | 96 | 118 | 6.0 |
| 8 | 104 | 120 | 6.0 |
| 9 | 104 | 120 | 6.0 |
| 10 | 106 | 120 | 6.0 |
| 11 | 106 | 120 | 6.0 |
| 12 | 107 | 122 | 6.0 |
| 13 | 108 | 123 | 6.0 |
| 14 | 109 | 125 | 6.0 |
| 15 | 110 | 127 | 6.0 |
| 16 | 112 | 132 | 6.0 |
| 17 | 113 | 134 | 6.0 |
| 18 | 115 | 135 | 6.0 |

-continued

| Fraction No. | Vapor Temp. (°C.) | Liquid Temp. (°C.) | Vacuum mm/Hg. Pressure |
|---|---|---|---|
| 19 | 120 | 141 | 6.0 |
| 20 | 127 | 144 | 6.0 |
| 21 | 132 | 148 | 6.0 |
| 22 | 135 | 155 | 6.0 |
| 23 | 135 | 172 | 6.0 |
| 24 | 135 | 190 | 6.0 |

Distillation fractions 10–17 are bulked. Distillation fractions 10–17 has a myrrh-like, olibanum-like, balsamic, peppery, fruity and smokey aroma profile, with myrrh, olibanum, honey-like, fruity, ozoney and leathery topnotes.

The resulting product contains the compounds having the structures

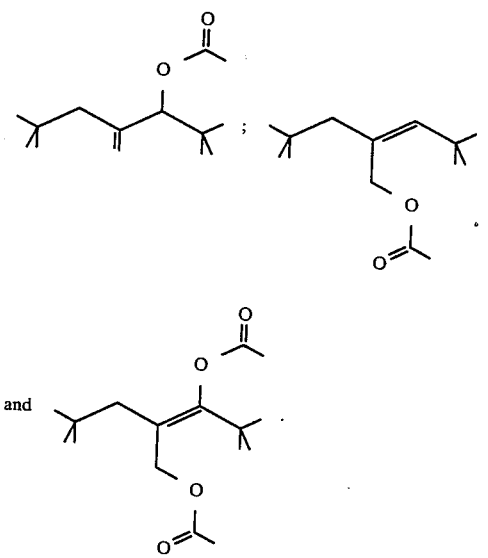

FIG. 4 is the GLC profile for the reaction product (Conditions: SE-30 column programmed at 150° C. isothermal). The peaks indicated by reference numerals 41 and 43 are the peaks for the compounds having the structures:

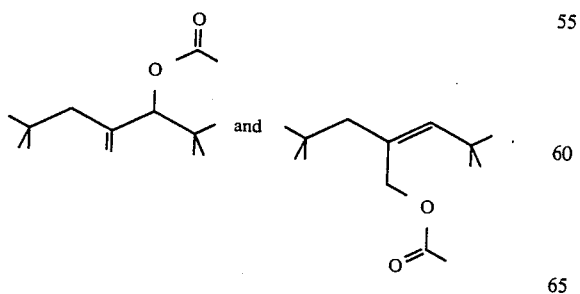

The peaks indicated by reference numerals 45 and 47 are for the compound having the structure:

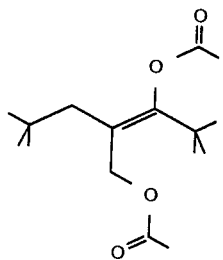

FIG. 5 is the NMR spectrum for the mixture of compounds having the structures:

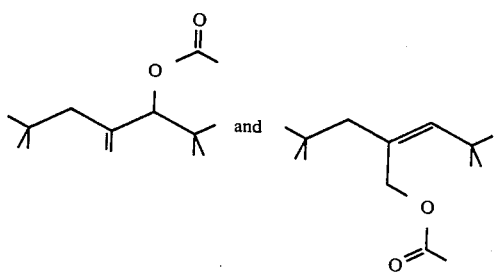

FIG. 6 is the NMR spectrum for the compound having the structure:

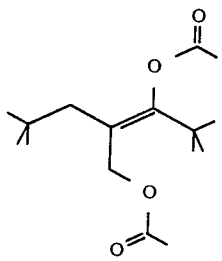

EXAMPLE III

Preparation of Triisobutylene Alcohol Mixture

Reaction:

Na⊕OH⊖ + 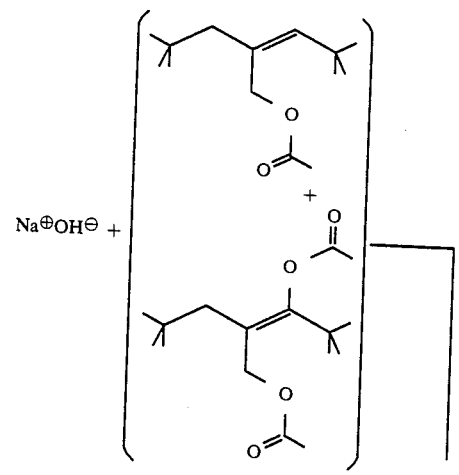

-continued

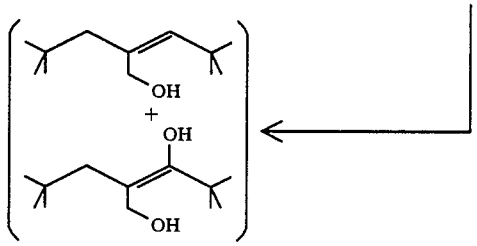

(and in addition, the compound having the structure:

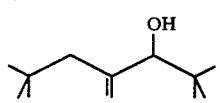

is also produced as part of the mixture).

Into a 2 liter reaction vessel is placed 495 grams of the triisobutylene acetate prepared according to Example II, 320 grams of 50% aqueous sodium hydroxide, 100 grams of methyl alcohol and 125 grams of water. The resulting mixture is heated to reflux (92° C.) and maintained at reflux for a period of three hours.

At the end of the three hour period, the reaction mass is cooled to 50° C. and washed with a 10% sodium chloride solution. The resulting reaction product is then fractionally distilled yielding the following fractions:

| Fraction No. | Vapor Temp. (°C.) | Liquid Temp. (°C.) | Vacuum mm/Hg. Pressure |
|---|---|---|---|
| 1 | 23/88 | 23/100 | 3.0 |
| 2 | 88 | 100 | 3.0 |
| 3 | 88 | 100 | 3.0 |
| 4 | 88 | 100 | 3.0 |
| 5 | 88 | 102 | 3.0 |
| 6 | 88 | 102 | 3.0 |
| 7 | 89 | 102 | 3.0 |
| 8 | 89 | 102 | 3.0 |
| 9 | 89 | 102 | 3.0 |
| 10 | 89 | 108 | 3.0 |
| 11 | 89 | 100 | 3.0 |
| 12 | 89 | 100 | 3.0 |
| 13 | 88 | 118 | 3.0 |
| 14 | 90 | 185 | 3.0 |

Distillation fractions 5–12 are bulked and the bulked distillation fractions 5–12 have a rose, geranium, peppery, herbaceous and fruity aroma, with fresh, peppery, rose, geranium, minty, fruity and green topnotes.

FIG. 7 is the GLC profile of the reaction product. The peaks indicated by reference numerals 70 and 72 are the peaks for the compounds having the structures:

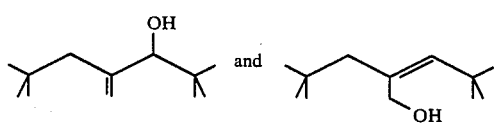

FIG. 8 is the NMR spectrum for the compounds having the structures:

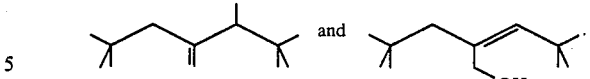

EXAMPLE IV

Preparation of Triisobutylene Propionate Composition

Reaction:

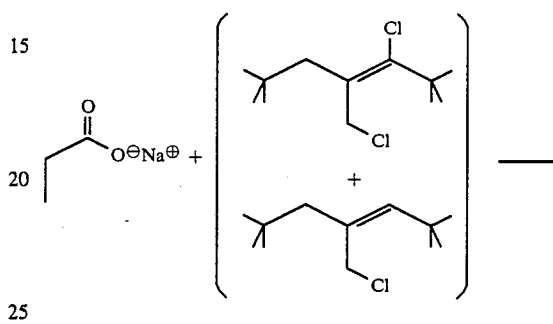

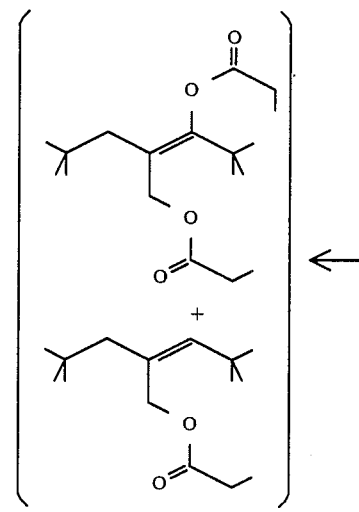

(reaction product also includes the compound having the structure:

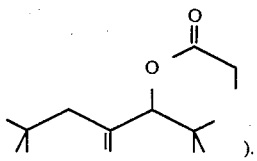).

Into a 5 liter reaction vessel equipped with stirrer, thermometer and reflux condenser is placed 2000 grams of the triisobutylene chloride prepared according to Example I and 1152 grams of sodium propionate.

The reaction mass is heated with stirring to 170° C. and maintained at 170° C. for a period of fifteen hours.

At the end of the fifteen hour period, the reaction mass is washed with 5 liters of water followed by 10% sodium bicarbonate solution.

The resulting product is then distilled yielding the following fractions:

| Fraction No. | Vapor Temp. (°C.) | Liquid Temp. (°C.) | Vacuum mm/Hg. Pressure |
|---|---|---|---|
| 1 | 23/92 | 23/120 | 10.0 |
| 2 | 92 | 132 | 10.0 |
| 3 | 118 | 130 | 10.0 |
| 4 | 118 | 138 | 10.0 |
| 5 | 118 | 138 | 10.0 |
| 6 | 118 | 138 | 8.0 |
| 7 | 118 | 142 | 8.0 |
| 8 | 118 | 142 | 8.0 |
| 9 | 118 | 144 | 8.0 |
| 10 | 122 | 149 | 8.0 |
| 11 | 122 | 149 | 8.0 |
| 12 | 122 | 155 | 8.0 |
| 13 | 127 | 162 | 8.0 |
| 14 | 133 | 168 | 8.0 |
| 15 | 137 | 173 | 8.0 |
| 16 | 140 | 175 | 8.0 |
| 17 | 147 | 178 | 8.0 |
| 18 | 153 | 182 | 8.0 |
| 19 | 144 | 182 | 5.0 |
| 20 | 143 | 190 | 3.0 |
| 21 | 143 | 200 | 3.0 |

Fraction 11 of the foregoing distillation contains the compounds having the structures:

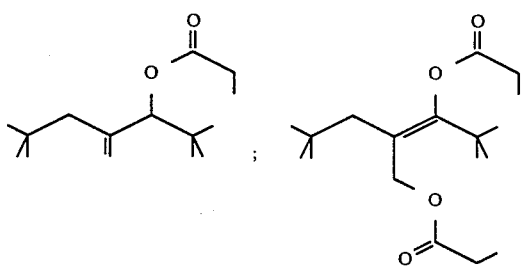

and

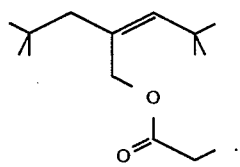

Fraction 11 has an olibanum resin-like, myrrh-like, woody and linseed oil-like aroma with leathery undertones.

FIG. 9 is the NMR spectrum for the compound having the structure:

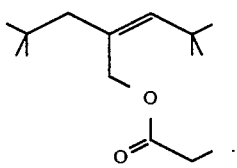

FIG. 10 is the NMR spectrum for the compound having the structure:

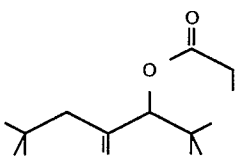

EXAMPLE V

Woody Perfume Compositions

The triisobutylene alcohols and esters produced according to Examples I, II, III and IV have use in altering, augmenting or enhancing such fragrances as the following pine/musk fragrance. In each of the cases, the triisobutylene alcohols and esters are used in an amount of 47.9%:

| Ingredients | Parts by Weight EXAMPLE | | | |
|---|---|---|---|---|
| | V(A) | V(B) | V(C) | V(D) |
| Isobornyl acetate | 100 | 100 | 100 | 100 |
| Camphor | 10 | 10 | 10 | 10 |
| Terpineol | 25 | 25 | 25 | 25 |
| Fir Balsam Absolute (50% in Diethyl Phthalate) | 20 | 20 | 20 | 20 |
| Coumarin | 4 | 4 | 4 | 4 |
| Linalool | 30 | 30 | 30 | 30 |
| Anethol | 2 | 2 | 2 | 2 |
| Fenchyl Alcohol | 10 | 10 | 10 | 10 |
| Lemon Terpenes Washed | 50 | 50 | 50 | 50 |
| Borneol | 5 | 5 | 5 | 5 |
| Galbanum Oil | 5 | 5 | 5 | 5 |
| Turpentine Russian | 150 | 150 | 150 | 150 |
| *Pinus Pumilionus* | 50 | 50 | 50 | 50 |
| Eucalyptol | 50 | 50 | 50 | 50 |
| 2,2,6-Trimethyl-1-cyclohexene-1-carboxaldehyde | 5 | 5 | 5 | 5 |
| Maltol 1% in Diethyl Phthalate | 10 | 10 | 10 | 10 |
| Mixture of compounds having the structures: and prepared according to Example II, bulked distillation fractions 10-17. | 470 | 0 | 0 | 0 |

Mixture of compounds having the structures:

-continued

| Ingredients | Parts by Weight EXAMPLE | | | |
|---|---|---|---|---|
| | V(A) | V(B) | V(C) | V(D) |
| 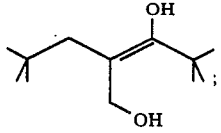 and 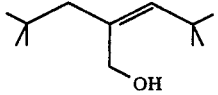 prepared according to Example III, bulked distillation fractions 5-12. Mixture of compounds having the structures: | 0 | 480 | 0 | 240 |
| 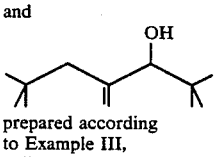 and  prepared according to Example IV, distillation fraction 11. | 0 | 0 | 480 | 240 |

The perfume composition of Example V(A) as a result of adding thereto the reaction product of Example II can be described as "pine/musk aroma with a myrrh, olibanum, balsamic, peppery, fruity and smokey undertone and myrrh, olibanum, honey-like, fruity, ozoney and leathery topnotes".

The perfume composition of Example V(B) can be described as "pine/musk aroma with rose, geranium, peppery, herbaceous and fruity undertones and fresh, peppery, rose, geranium, minty, fruity and green topnotes".

The perfume composition of Example V(C) can be described as "pine/musk aroma with olibanum resin-like, myrrh-like, woody, linseed oil-like topnotes and leathery undertones".

The perfume composition of Example V(D) can be described as "a pine/musk aroma with rose, geranium, peppery, herbaceous, fruity and leathery undertones and fresh, peppery, rose, geranium, minty, fruity, green, olibanum, myrrh, woody and linseed oil topnotes".

EXAMPLE VI

Preparation of a Cosmetic Powder

A cosmetic powder is prepared by mixing in a ball mill, 100 grams of talcum powder with 0.25 grams of one of the products listed below of our invention. The resulting material has an excellent perfume aroma as set forth in the table below:

TABLE II

| Description of Composition | Fragrance Characteristics |
|---|---|
| A. The mixture of compounds having the structures: 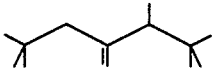  and 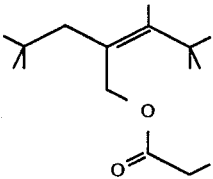 prepared according to Example II, bulked distillation fractions 10-17. | A myrrh-like, olibanum-like, balsamic, peppery, fruity and smokey aroma profile with myrrh, olibanum, honey-like, fruity, ozoney and leathery topnotes. |
| B. Mixture of compounds having the structures: 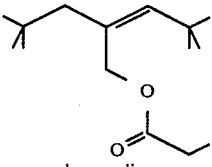 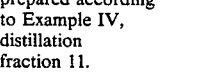 and  prepared according to Example III, bulked distillation fractions 5-12. | A rose, geranium, peppery, herbaceous and fruity aroma profile with fresh, peppery, rose, geranium, minty, fruity and green topnotes. |
| C. Mixture of compounds having the structures: | An olibanum resin-like, myrrh-like, woody and linseed oil-like |

TABLE II-continued

| Description of Composition | Fragrance Characteristics |
|---|---|
| 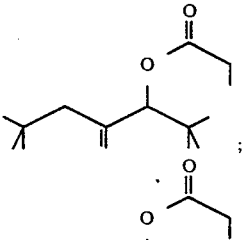 prepared according to Example IV, distillation fraction 11. | aroma profile with leathery undertones. |
| Perfume composition of Example V(A). | Pine/musk aroma with a myrrh, olibanum, balsamic, peppery, fruity and smokey undertone and myrrh, olibanum, honey-like, fruity, ozoney and leathery topnotes. |
| Perfume composition of Example V(B). | Pine/musk aroma with rose, geranium, peppery, herbaceous and fruity undertones and fresh, peppery, rose, geranium, minty, fruity and green topnotes. |
| Perfume composition of Example V(C). | Pine/musk aroma with olibanum resin-like, myrrh-like, woody, linseed oil-like topnotes and leathery undertones. |
| Perfume composition of Example V(D). | A pine/musk aroma with rose, geranium, peppery, herbaceous, fruity and leathery undertones and fresh, peppery, rose, geranium, minty, fruity, green, olibanum, myrrh, woody and linseed oil topnotes. |

EXAMPLE VII

Perfumed Liquid Detergents

Concentrated liquid detergents with aromas as set forth in Table II of Example VI, supra, (which detergents are produced from the Lysine salt of n-dodecyl benzene sulfonic acid, as more specifically described in U.S. Pat. No. 3,948,818, issued on Apr. 6, 1976) are prepared containing the perfume materials as set forth in Table II of Example VI, supra. They are prepared by adding and homogeneously admixing the appropriate quantity of perfume material in the liquid detergent. The detergents all possess excellent aromas as set forth in Table II of Example VI, supra.

EXAMPLE VIII

Preparation of a Cologne and Handkerchief Perfume

Perfume compositions and substances as indicated in Table II of Example VI, supra, are incorporated into colognes at concentrations of 1.5%, 2.0%, 2.5%, 3.0%, 3.5%, 4.0% and 5.0% in 80%, 85%, 90% and 95% aqueous food grade ethanol; and into handkerchief perfumes at concentrations of 10%, 15%, 20%, 30%, 40% and 50% (in 90% and 95% aqueous food grade ethanol). Distinct and definitive fragrance aromas as set forth in Table II of Example VI, supra, are imparted to the colognes and to the handkerchief perfumes.

EXAMPLE IX

Preparation of Soap Composition

One hundred grams of soap chips (obtained from IVORY®-Soap) (a trademark of Procter & Gamble Company of Cincinnati, Ohio) are mixed with two grams of each of the materials (separately as set forth in Table II of Example VI, supra, until a substantially homogeneous composition is obtained in each of the six cases. The resulting compositions are each individually melted at 180° C. for a period of four hours under 8 atmospheres nitrogen pressure. The resulting melt are cooled and formed into soap bars. Each of the soap bars has an aroma as set forth in Table II of Example VI, supra.

EXAMPLE X

Preparation of Liquid Detergent

Concentrated liquid detergents with aromas as set forth in Table II of Example VI, supra, containing 0.2%, 0.5% and 1.2% of the perfume composition and substances as set forth in Table II of Example VI are prepared by adding the appropriate quantity of the indicated composition as set forth in Table II of Example VI to a liquid detergent known as P-87. The aromas of the liquid detergent increase with increasing composition of the perfumery composition as set forth in Table II of Example VI, supra.

EXAMPLE XI

Utilizing the procedure of Example I of Column 15 of U.S. Pat. No. 3,632,396 (the disclosure and specification which is incorporated herein by reference) a nonwoven cloth substrate useful as a drier-added fabric softening article of manufacture is prepared wherein the substrate, the substrate coating and the outer coating and the perfuming material are as follows:
1. a water "dissolve" paper ("Dissolvo Paper");
2. Adogen 448 (m.p. about 140° F.) as the substrate coating; and
3. an outer coating having the following formulation (m.p. about 150° F.);
   57% — $C_{20-22}$ HAPS
   22% — isopropyl alcohol
   20% — antistatic agent
1% of a perfumery substance as set forth in Table II of Example VI, supra, having aroma properties as set forth in Table II of Example VI, supra.

Fabric softening compositions prepared as set forth above having the aroma characteristics as set forth in Table II of Example VI, supra, essentially consist of a substrate having the weight of about 3 grams per 100 square inches, a substrate coating of about 1.85 grams per 100 square inches of substrate, and an outer coating of about 1.4 grams per 100 square inches of substrate, thereby providing a total aromatized substrate and outer coating weight ratio of about 1:1 by weight of the substrate. The aromas as set forth in Table II of Example VI, supra, are imparted in a pleasant manner to the head space in the dryer on operation thereof using the said drier-added fabric softening nonwoven fabric article.

EXAMPLE XII

Hair Spray Formulations

The following hair spray formulation is prepared by first dissolving PVP/VA E-735 copolymer manufactured by the GAF Corporation of 140 West 51st Street, New York, N.Y., in 91.62 grams of 95% food grade ethanol. 8.0 Grams of the polymer is dissolved in the alcohol. The following ingredients are added to the PVP/VA alcoholic solution:

| Ingredients | Weight Percent |
| --- | --- |
| Dioctyl sebacate | 0.05 |
| Benzyl alcohol | 0.10 |
| Dow Corning 473 fluid (prepared by the Dow Corning Corporation) | 0.10 |
| TWEEN ® 20 surfactant (prepared by ICI America Corporation) | 0.03 |
| One of the perfumery substances as set forth in Table II of Example VI, supra. | 0.10 |

The perfume substances as set forth in Table II of Example VI add aroma characteristics as set forth in Table II of Example VI which are rather intense and aesthetically pleasing to the users of the soft-feel, good hold pump hair sprays.

EXAMPLE XIII

Conditioning Shampoos

Monamid CMA (prepared by the Mona Industries Company) (3.0 weight percent) is melted with 2.0 weight percent coconut fatty acid (prepared by Procter & Gamble Company of Cincinnati, Ohio); 1.0 weight percent ethylene glycol distearate (prepared by the Armak Corporation) and triethanolamine (a product of Union Carbide Corporation) (1.4 weight percent). The resulting melt is admixed with Stepanol WAT produced by the Stepan Chemical Company (35.0 weight percent). The resulting mixture is heated to 60° C. and mixed until a clear solution is obtained (at 60° C.). This material is "COMPOSITION A".

GAFQUAT ®755N polymer (manufactured by GAF Corporation of 140 West 51st Street, New York, N.Y.) (5.0 weight percent) is admixed with 0.1 weight percent sodium sulfite and 1.4 weight percent polyethylene glycol 6000 distearate produced by Armak Corporation. This material is "COMPOSITION B".

The resulting "COMPOSITION A" and "COMPOSITION B" are then mixed in a 50:50 weight ratio of A:B and cooled to 45° C. and 0.3 weight percent of perfuming substances as set forth in Table II of Example VI is added to the mixture. The resulting mixture is cooled to 40° C. and blending is carried out for an additional one hour in each case. At the end of the one hour period, the resulting material has a pleasant fragrance as indicated in Table II of Example VI.

EXAMPLE XIV

Each of the fragrance materials of Table II of Example VI, supra, are added to a 50:50 weight:weight mixture of low density polyethylene:polyepsilon caprolactone PCL-700 forming pellets with scents as set forth in Table II of Example VI, supra.

75 Pounds of a 50:50 mixture of PCL-700 polyepsilon caprolactone (manufactured by the Union Carbide Corporation of New York, N.Y. having a melting point of about 180°-190° F.): Low density polyethylene, are heated to about 250° F. in a container of the kind illustrated in FIGS. 11 and 12. 25 Pounds of each of the fragrance materials as set forth in Table II of Example VI, is then quickly added to the liquified polymer mixture, the lid 228 is put in place and the agitating means 273 are actuated. The temperature is then raised to about 260° F. and the mixing is continued for 5-15 minutes. The valve "V" is then opened to allow flow of the molten polymer enriched with perfume ingredient to exit through the orifices 234. The liquid falling through the orifices 234 solidifies almost instantaneously upon impact with the moving cooled conveyor 238. Polymer beads or pellets 244 having pronounced scents as described in Table II of Example VI, supra, are thus formed. Analysis demonstrates that the pellets contain about 25% of the perfume material so that almost no losses in the scenting substance did occur. These pellets may be called "master pellets".

50 Pounds of each batch of the scent containing "master pellets" are then added to one thousand pounds of unscented polypropylene and the mass is heated to the liquid state. The liquid is molded into thin sheets of films. The thin sheets of films have pronounced aromas as set forth in Table II of Example VI, supra. The sheets of films are cut into strips of 0.25" in width×3" in length and placed into room air fresheners.

On operation of the room air freshener, after four minutes, the room in each case has an aesthetically pleasing aroma with no foul odor being present, the aroma being described in Table II of Example VI, supra.

What is claimed is:

1. At least one triisobutylene alcohol or ester having the structure:

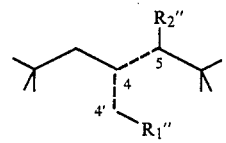

wherein one of the dashed lines is a carbon-carbon double bond and the other of the dashed lines is a carbon-carbon single bond; wherein $R_1''$ and $R_2''$ are the same or different and each represents hydrogen, hydroxyl or a $C_1$-$C_3$ acyloxy with the provisos that:

(i) when the carbon-carbon bond at the 4—4' position is a double bond, then $R_1''$ is hydrogen; and (ii) $R_1''$ and $R_2''$ are not both hydrogen.

2. A mixture of two or more compounds defined according to claim 1.

3. The mixture of claim 2 containing the compounds having the structures:

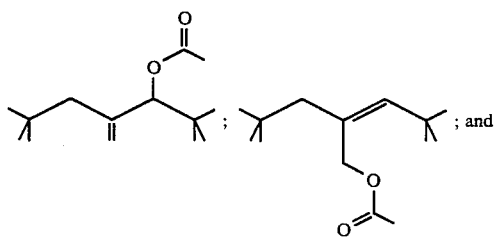 ; and

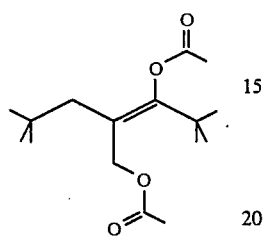.

4. The mixture of compounds of claim 2 having the structures:

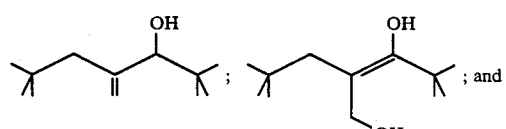 ; and

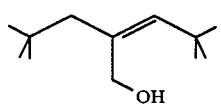.

5. The mixture of compounds of claim 2 having the structures:

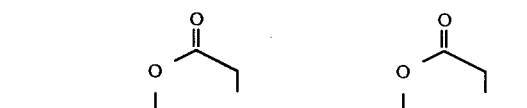 ; and

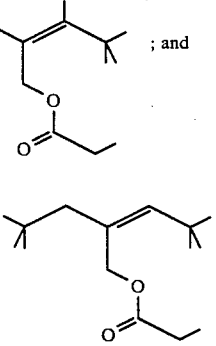.

6. The product produced according to the process comprising the steps of:

(i) reacting a halogen with triisobutylene according to the reaction:

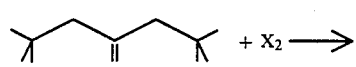

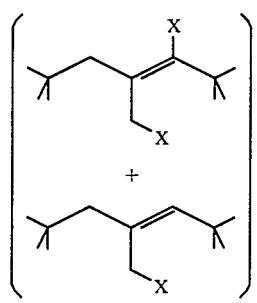

(ii) reacting the resulting mixture of halogenated triisobutylenes with an alkali metal acylate according to the reaction:

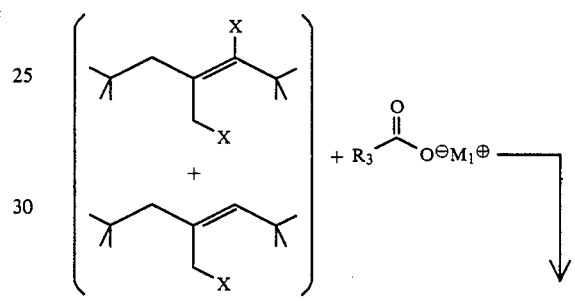

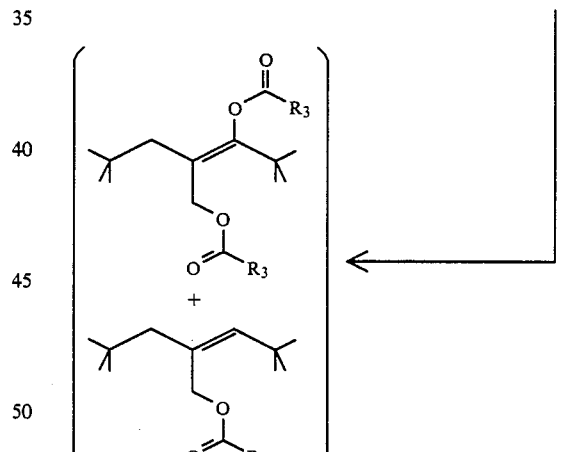

wherein $R_3$ is hydrogen or $C_1$ or $C_2$ alkyl; and wherein $M_1$ represents sodium or potassium.

7. The product produced according to the process comprising the steps of:

(i) reacting a halogen with triisobutylene according to the reaction:

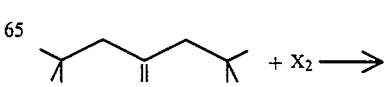

-continued

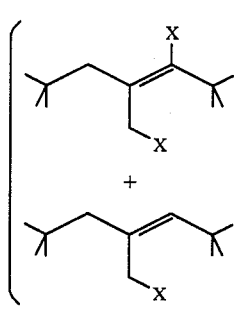
+
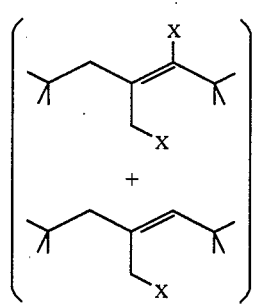

(ii) reacting the resulting mixture of halogenated triisobutylenes with an alkali metal acylate according to the reaction:

-continued

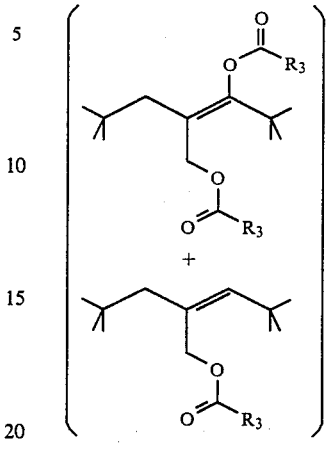

wherein $R_3$ is hydrogen or $C_1$ or $C_2$ alkyl; and wherein $M_1$ represents sodium or potassium; and
(iii) hydrolyzing the resulting ester mixture with base according to the reaction:

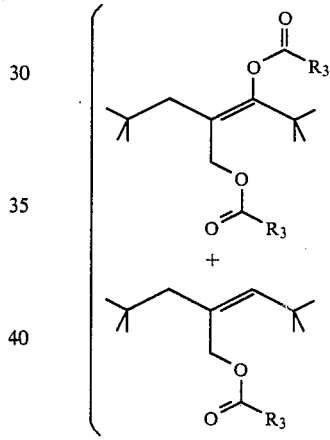 $+ M_2^\oplus OH^\ominus \longrightarrow$

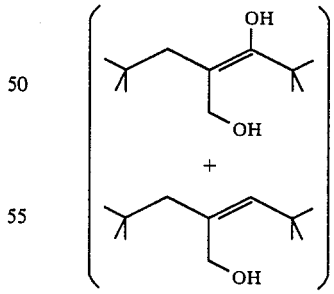

wherein $M_2$ represents sodium or potassium and $R_3$ is hydrogen or $C_1$–$C_2$ alkyl.

* * * * *

$+ R_3\overset{O}{\underset{}{\text{C}}}-O^\ominus M_1^\oplus \longrightarrow$